US007960089B2

(12) United States Patent
Shiono et al.

(10) Patent No.: US 7,960,089 B2
(45) Date of Patent: Jun. 14, 2011

(54) COMPOUND, METHOD FOR PRODUCING SAME, POSITIVE RESIST COMPOSITION AND METHOD FOR FORMING RESIST PATTERN

(75) Inventors: Daiju Shiono, Kawasaki (JP); Takahiro Dazai, Kawasaki (JP); Taku Hirayama, Kawasaki (JP); Kohei Kasai, Kawasaki (JP); Hideo Hada, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 466 days.

(21) Appl. No.: 12/067,255

(22) PCT Filed: Sep. 13, 2006

(86) PCT No.: PCT/JP2006/318151
§ 371 (c)(1),
(2), (4) Date: Mar. 18, 2008

(87) PCT Pub. No.: WO2007/034719
PCT Pub. Date: Mar. 29, 2007

(65) Prior Publication Data
US 2010/0183974 A1    Jul. 22, 2010

(30) Foreign Application Priority Data

| Sep. 20, 2005 | (JP) | 2005-271760 |
| Nov. 4, 2005 | (JP) | 2005-320550 |
| Nov. 4, 2005 | (JP) | 2005-320551 |
| Mar. 20, 2006 | (JP) | 2006-076270 |
| Jun. 16, 2006 | (JP) | 2006-167263 |
| Sep. 5, 2006 | (JP) | 2006-239982 |

(51) Int. Cl.
G03F 7/004 (2006.01)
C07C 39/12 (2006.01)
(52) U.S. Cl. ............... 430/270.1; 430/326; 568/720
(58) Field of Classification Search ............... 430/270.1, 430/326; 568/720
See application file for complete search history.

(56) References Cited

U.S. PATENT DOCUMENTS

| 5,945,517 | A |   | 8/1999 | Nitta et al. |   |
| 6,180,313 | B1 |   | 1/2001 | Yukawa et al. |   |
| 7,504,196 | B2 | * | 3/2009 | Shiono et al. | 430/270.1 |
| 7,659,047 | B2 | * | 2/2010 | Kojima et al. | 430/270.1 |
| 2008/0113294 | A1 | * | 5/2008 | Echigo et al. | 430/270.1 |
| 2008/0145784 | A1 | * | 6/2008 | Shiono et al. | 430/281.1 |

FOREIGN PATENT DOCUMENTS

| JP | 09-208554 | 8/1997 |
| JP | 11-35551 | 2/1999 |
| JP | 11-35552 | 2/1999 |
| JP | 11-35573 | 2/1999 |
| JP | 11-322707 | 11/1999 |
| JP | 2001-312055 | * 9/2001 |
| JP | 2001-312055 | 11/2001 |
| JP | 2006-039281 | 2/2006 |
| JP | 2006-267996 | 10/2006 |
| WO | WO 2004-074242 | 9/2004 |

OTHER PUBLICATIONS

Hirayama et al., Journal of Photopolymer Science and Technology, vol. 17 No. 3, pp. 435-440, (2004). Kim et al., *Novel Molecular Resist Based on Derivative of Cholic Acid*, Chemistry Letters, pp. 1064-1065, (2002).
International Search Report in connection with corresponding PCT application No. PCT/JP2006/318151, dated Nov. 28, 2006.

* cited by examiner

*Primary Examiner* — John S Chu
(74) *Attorney, Agent, or Firm* — Knobbe, Martens, Olson & Bear, LLP

(57) ABSTRACT

A compound of the present invention is a compound represented by a general formula (A-1) [wherein, R' represents a hydrogen atom or an acid-dissociable, dissolution-inhibiting group, provided that at least one R' group is an acid-dissociable, dissolution-inhibiting group, $R^{11}$ to $R^{17}$ each represent an alkyl group of 1 to 10 carbon atoms or an aromatic hydrocarbon group, which may include a hetero atom within the structure; g and j each represent an integer of 1 or greater, and k and q each represent an integer of 0 or greater, provided that g+j+k+q is not greater than 5; a represents an integer from 1 to 3; b represents an integer of 1 or greater, and l and m each represent an integer of 0 or greater, provided that b+l+m is not greater than 4; c represents an integer of 1 or greater, and n and o each represent an integer of 0 or greater, provided that c+n+o is not greater than 4; and A represents a group represented by a general formula (Ia) shown below, a group represented by a general formula (Ib) shown below, or an aliphatic cyclic group].

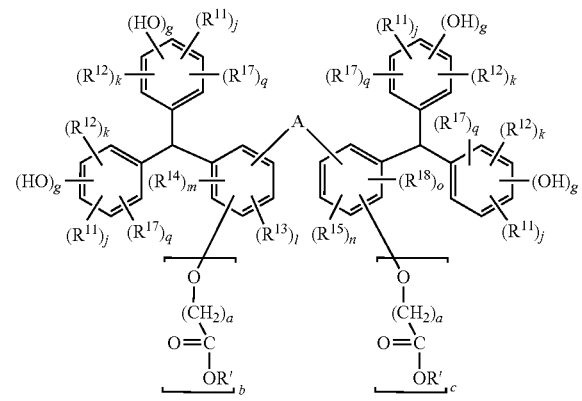

11 Claims, No Drawings

COMPOUND, METHOD FOR PRODUCING SAME, POSITIVE RESIST COMPOSITION AND METHOD FOR FORMING RESIST PATTERN

RELATED APPLICATIONS

This application is the U.S. National Phase filing under 35 U.S.C. §371 of PCT/JP2006/318151, filed Sep. 13, 2006, which designated the United States and was published in a language other than English, which claims priority under 35 U.S.C. §119(a)-(d) to Japanese Patent Application No. 2006-239982, filed Sep. 5, 2006, Japanese Patent Application No. 2006-167263, filed Jun. 16, 2006, Japanese Patent Application No. 2006-076270, filed Mar. 20, 2006, Japanese Patent Application No. 2005-320551, filed Nov. 4, 2005, Japanese Patent Application No. 2005-320550, filed Nov. 4, 2005, and Japanese Patent Application No. 2005-271760, filed Sep. 20, 2005. The contents of these applications are incorporated herein by reference in their entireties.

TECHNICAL FIELD

The present invention relates to a compound that can be used within a resist composition, a positive resist composition that includes the compound, and a method for forming a resist pattern that uses the positive resist composition.

Furthermore, the present invention also relates to a compound that can be used favorably for the production of a low molecular weight compound that can be used within a resist composition, and a method for producing the compound.

BACKGROUND ART

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultra violet radiation typified by g-line and i-line radiation has been used, but nowadays, mass production of semiconductor elements using KrF excimer lasers and ArF excimer lasers has commenced. Furthermore, investigation is also being conducted into radiation with even shorter wavelengths than these excimer lasers, including $F_2$ excimer lasers, electron beams, EUV (extreme ultra violet), and X-rays.

Furthermore, one example of a known pattern-forming material capable of forming a pattern of minute dimensions is a chemically amplified resist, which includes a base material component with a film-forming capability, and an acid generator component that generates acid upon exposure. Chemically amplified resists include negative resists, which undergo a reduction in alkali solubility upon exposure, and positive resists, which display increased alkali solubility upon exposure.

Conventionally, polymers have been used as the base material components within these types of chemically amplified resists, and examples of these polymers include polyhydroxystyrene (PHS), PHS-based resins in which a portion of the hydroxyl groups of a PHS have been protected with acid-dissociable, dissolution-inhibiting groups, copolymers derived from (meth)acrylate esters, and resins in which a portion of the carboxyl groups within these (meth)acrylate esters have been protected with acid-dissociable, dissolution-inhibiting groups.

However, when a pattern is formed using these types of pattern-forming materials, a problem arises in that roughness can develop on the upper surface and side wall surfaces of the pattern. For example, roughness on the side wall surfaces of a resist pattern, so-called line edge roughness (LER), can cause distortions around the holes in hole patterns, and fluctuations in the line width in line and space patterns, and consequently has the potential to adversely affect the formation of very fine semiconductor elements.

This problem becomes more significant as the pattern dimensions are reduced. Accordingly, in lithography processes using electron beams or EUV or the like, which are targeting the formation of very fine patterns with dimensions of several tens of nm, very low levels of roughness that are superior to current levels of pattern roughness are being demanded.

However, the polymers typically used as base materials have a large molecular size (or root mean squared radius per molecule) of several nm. In the developing step of a pattern formation process, the solubility behavior of the resist with respect to the developing solution typically occurs in single molecule units of the base material component, meaning that as long as polymers are used as the base material component, further reductions in the level of roughness will remain extremely difficult to achieve.

In order to overcome this type of problem, resists that employ a low molecular weight material as the base material component have been proposed as potential materials for achieving lower levels of roughness. For example, non-patent references 1 and 2 propose low molecular weight materials that include alkali-soluble groups such as hydroxyl groups or carboxyl groups, wherein either a portion of, or all of, these groups have been protected with acid-dissociable, dissolution-inhibiting groups.

[Non-Patent Reference 1] T. Hirayama, D. Shiono, H. Hada and J. Onodera: J. Photopolym. Sci. Technol., 17 (2004), p. 435

[Non-Patent Reference 2] Jim-Baek Kim, Hyo-Jin Yun, Young-Gil Kwon: Chemistry Letters (2002), pp. 1064 to 1065.

DISCLOSURE OF INVENTION

Problems to be Solved by the Invention

These types of low molecular weight materials have small molecular sizes as a result of their lower molecular weight, and as such, are expected to enable reductions in the level of roughness. Accordingly, there are now considerable demands for novel low molecular weight materials that can be used for resist compositions. Furthermore, there are also growing demands for low molecular weight materials which, when used within a resist composition, enable the formation of resist patterns that can be used in practical applications.

The present invention takes the above circumstances into consideration, with a first object of providing a compound that can be used within a resist composition, a positive resist composition containing the compound, and a method for forming a resist pattern that uses the positive resist composition.

Furthermore, the present invention has a second object of providing a compound that can be used favorably for the production of a low molecular weight compound that can be used within a resist composition, and a method for producing the compound.

Means for Solving the Problems

In order to achieve the above objects, a first aspect of the present invention is a compound represented by a general formula (A-1) shown below.

[Formula 1]

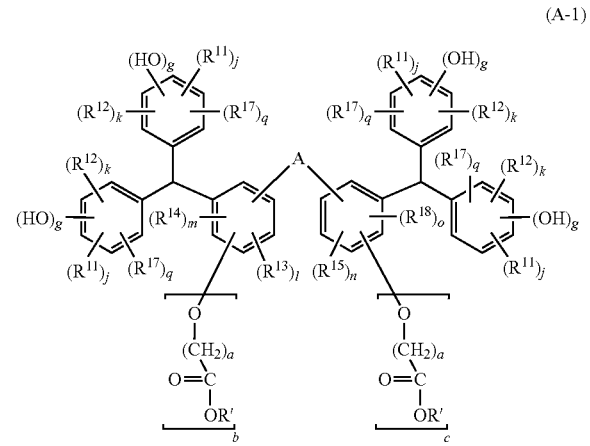

[In the formula (A-1), R' represents a hydrogen atom or an acid-dissociable, dissolution-inhibiting group, provided that at least one of the plurality of R' groups is an acid-dissociable, dissolution-inhibiting group, $R^{11}$ to $R^{17}$ each represent, independently, an alkyl group of 1 to 10 carbon atoms or an aromatic hydrocarbon group, which may include a hetero atom within the structure; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group.]

[Formula 2]

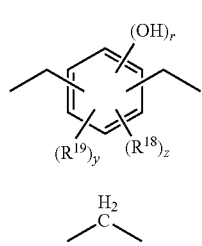

[In the formula (Ia), $R^{18}$ and $R^{19}$ each represent, independently, an alkyl group of 1 to 10 carbon atoms or an aromatic hydrocarbon group, which may include a hetero atom within the structure; and r, y and z each represent, independently, an integer of 0 or greater, provided that r+y+z is not greater than 4.]

Furthermore, a second aspect of the present invention is a positive resist composition that includes a base material component (A) that exhibits increased alkali solubility under the action of acid, and an acid generator component (B) that generates acid upon irradiation, wherein the base material component (A) contains a compound (A1) represented by a general formula (A-1) shown below.

[Formula 3]

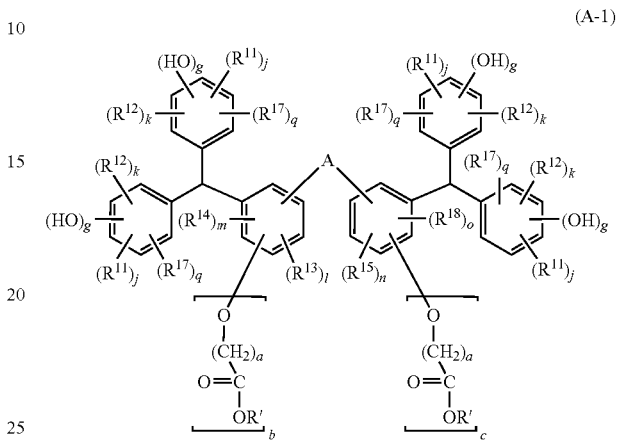

[In the formula (A-1), R' represents a hydrogen atom or an acid-dissociable, dissolution-inhibiting group, provided that at least one of the plurality of R' groups is an acid-dissociable, dissolution-inhibiting group, $R^{11}$ to $R^{17}$ each represent, independently, an alkyl group of 1 to 10 carbon atoms or an aromatic hydrocarbon group, which may include a hetero atom within the structure; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group.]

[Formula 4]

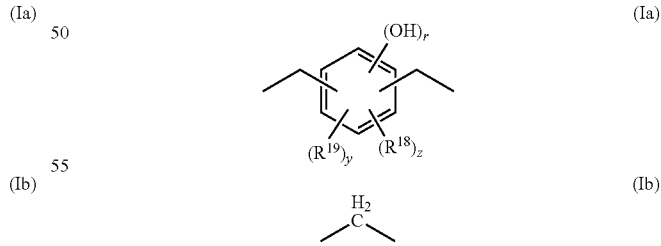

[In the formula (Ia), $R^{18}$ and $R^{19}$ each represent, independently, an alkyl group of 1 to 10 carbon atoms or an aromatic hydrocarbon group, which may include a hetero atom within the structure; and r, y and z each represent, independently, an integer of 0 or greater, provided that r+y+z is not greater than 4.]

Furthermore, a third aspect of the present invention is a method for forming a resist pattern that includes the steps of:

forming a resist film on a substrate using a positive resist composition according to the second aspect described above, exposing the resist film, and developing the resist film to form a resist pattern.

A fourth aspect of the present invention for achieving the objects described above is a compound represented by a general formula (I) shown below.

[Formula 5]

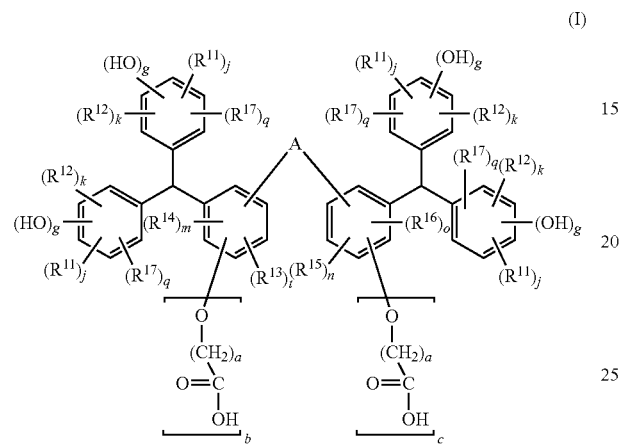

(I)

[In the formula (I), $R^{11}$ to $R^{17}$ each represent, independently, an alkyl group of 1 to 10 carbon atoms or an aromatic hydrocarbon group, which may include a hetero atom within the structure; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group.]

[Formula 6]

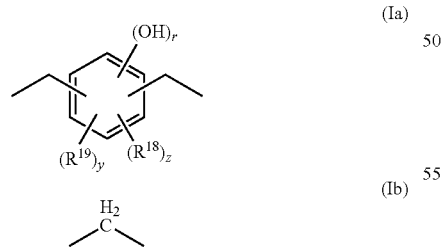

(Ia)

(Ib)

[In the formula (Ia), $R^{18}$ and $R^{19}$ each represent, independently, an alkyl group of 1 to 10 carbon atoms or an aromatic hydrocarbon group, which may include a hetero atom within the structure; and r, y and z each represent, independently, an integer of 0 or greater, provided that r+y+z is not greater than 4.]

Furthermore, a fifth aspect of the present invention is a method for producing a compound that includes:

a step of reacting a compound (I-1) represented by a general formula (I-1) shown below and a compound (I-2) represented by a general formula (I-2) shown below to obtain a compound (I-3) represented by a general formula (I-3) shown below, and a step of obtaining a compound represented by a general formula (I) shown below, via a step of reacting the compound (I-3) and a compound (I-4) represented by a general formula (I-4) shown below under acidic conditions.

[Formula 7]

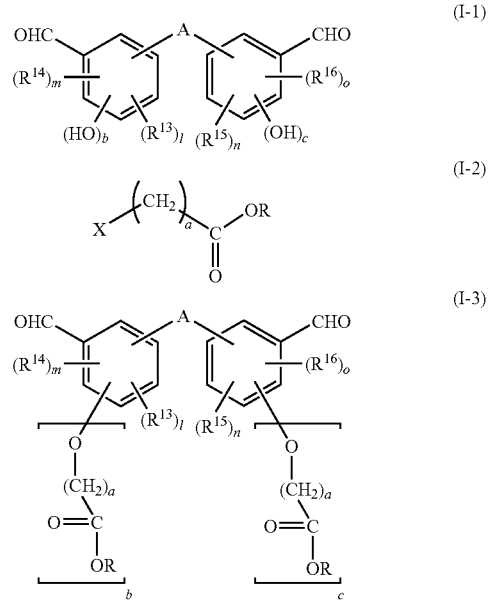

[wherein, X represents a halogen atom; R represents a protective group, $R^{13}$ to $R^{16}$ each represent, independently, an alkyl group of 1 to 10 carbon atoms or an aromatic hydrocarbon group, which may include a hetero atom within the structure; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group.]

[Formula 8]

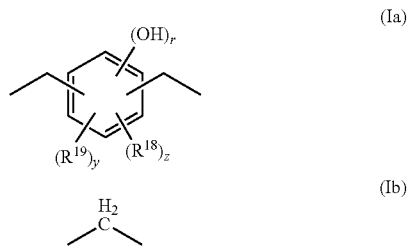

(Ia)

(Ib)

[In the formula (Ia), $R^{18}$ and $R^{19}$ each represent, independently, an alkyl group of 1 to 10 carbon atoms or an aromatic hydrocarbon group, which may include a hetero atom within the structure; and r, y and z each represent, independently, an integer of 0 or greater, provided that r+y+z is not greater than 4.]

[Formula 9]

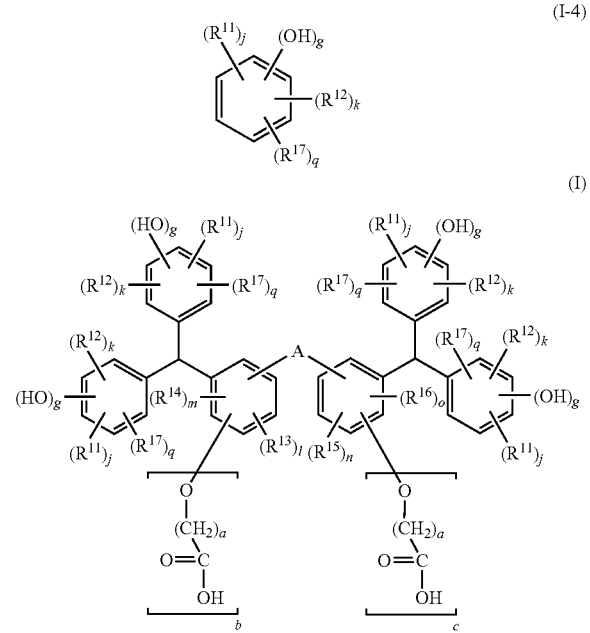

[wherein, $R^{11}$ to $R^{17}$ each represent, independently, an alkyl group of 1 to 10 carbon atoms or an aromatic hydrocarbon group, which may include a hetero atom within the structure; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown above, a group represented by a general formula (Ib) shown above, or an aliphatic cyclic group.]

Within the scope of the claims and the description of the present invention, unless stated otherwise, the term "alkyl group" includes straight-chain, branched and cyclic monovalent saturated hydrocarbon groups.

The term "aliphatic" is a relative concept used in relation to the term "aromatic", and defines a group or compound or the like that contains no aromaticity. The term "aliphatic cyclic group" describes a monocyclic group or polycyclic group that contains no aromaticity.

Furthermore, a "lower alkyl group" is preferably an alkyl group of 1 to 5 carbon atoms.

Effects of the Invention

According to the present invention, there are provided a compound that can be used within a resist composition, a positive resist composition that includes the compound, and a method for forming a resist pattern that uses the positive resist composition.

According to the present invention, there are also provided a compound that can be used favorably for the production of a low molecular weight compound that can be used within a resist composition, and a method for producing the compound.

BEST MODE FOR CARRYING OUT THE INVENTION

Compound of First Embodiment

A compound of a first embodiment of the present invention (hereafter referred to as the compound (A1)) is represented by the general formula (A-1) shown above.

In the general formula (A-1), R' represents a hydrogen atom or an acid-dissociable, dissolution-inhibiting group, provided that at least one of the plurality of R' groups is an acid-dissociable, dissolution-inhibiting group.

In the general formula (A-1), the acid-dissociable, dissolution-inhibiting group represented by R' is a group that exhibits an alkali dissolution-inhibiting effect that renders the compound (A1) insoluble in alkali prior to dissociation, but then upon dissociation, causes the compound (A1) to change to an alkali-soluble state. Accordingly, when the compound (A1) is blended into a positive resist composition, together with an acid generator component (B), in the manner described below, the action of the acid generated from the acid generator component (B) by exposure causes the acid-dissociable, dissolution-inhibiting groups to dissociate, thereby causing the compound (A1) to change from an alkali-insoluble state to an alkali-soluble state.

There are no particular restrictions on the acid-dissociable, dissolution-inhibiting group, which may be selected appropriately from those groups proposed for use within the hydroxystyrene-based resins and (meth)acrylate-based resins and the like used in chemically amplified positive resist compositions designed for use with KrF or ArF excimer lasers. Specific examples include tertiary alkyl groups, tertiary alkyloxycarbonyl groups, alkoxycarbonylalkyl groups, alkoxyalkyl groups, and cyclic ether groups. Here the term "(meth)acrylate" means either one of, or both, acrylate and methacrylate.

Specific examples of the tertiary alkyl groups include chain-like tertiary alkyl groups such as a tert-butyl group or tert-amyl group, and tertiary alkyl groups that contain an aliphatic cyclic group, such as a 2-methyl-2-adamantyl group or 2-ethyl-2-adamantyl group. Specific examples of the above aliphatic cyclic group include groups in which one or more hydrogen atoms have been removed from a monocycloalkane or a polycycloalkane such as a bicycloalkane, tricycloalkane or tetracycloalkane, which may, or may not, be substituted with a lower alkyl group, a fluorine atom or a fluoroalkyl group. Specific examples include groups in which one or more hydrogen atoms have been removed from either a monocycloalkane such as cyclopentane or cyclohexane, or a polycycloalkane such as adamantane, norbornane, isobornane, tricyclodecane or tetracyclododecane.

Examples of tertiary alkyl groups that contain an aliphatic cyclic group include groups that contain a tertiary carbon atom within the ring skeleton of an aliphatic cyclic group, such as the 2-methyl-2-adamantyl group and 2-ethyl-2-adamantyl group mentioned above; and groups in which a portion of the hydrogen atoms of a chain-like tertiary alkyl group have been substituted with the above type of aliphatic cyclic group.

Examples of the tertiary alkyl group within a tertiary alkyloxycarbonyl group, include the same tertiary alkyl groups as those listed above. Specific examples of the tertiary alkyloxycarbonyl groups include a tert-butyloxycarbonyl group and tert-amyloxycarbonyl group.

Specific examples of the cyclic ether groups include a tetrahydropyranyl group and tetrahydrofuranyl group.

In the present invention, compounds that include at least one acid-dissociable, dissolution-inhibiting group selected from the group consisting of alkoxycarbonylalkyl groups represented by a general formula (p1) shown below, and alkoxyalkyl groups represented by a general formula (p2) shown below are preferred as they yield superior effects for the present invention.

[Formula 10]

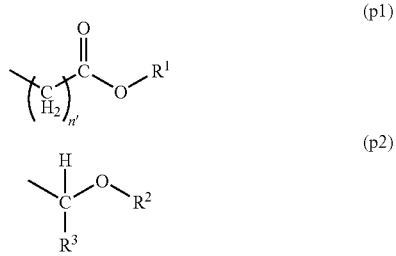

[wherein, $R^1$ and $R^2$ each represent, independently, a straight-chain, branched or cyclic alkyl group, which may include a hetero atom within the structure; $R^3$ represents a hydrogen atom or a lower alkyl group; and n' represents an integer from 1 to 3.]

In the general formula (p1), n' represents an integer from 1 to 3, and is most preferably 1.

$R^1$ represents a straight-chain, branched or cyclic alkyl group, which may include a hetero atom within the structure. In other words, in the alkyl group represented by $R^1$, either a portion of, or all of, the hydrogen atoms may be substituted with a group that contains a hetero atom (including those cases where the hetero atom itself functions as the substituent group), or a portion of the carbon atoms of the alkyl group may be substituted with a hetero atom.

Examples of the hetero atom include an oxygen atom, sulfur atom, nitrogen atom, and fluorine atom.

A "group that contains a hetero atom" may be the hetero atom itself, or a group that contains the hetero atom and a carbon atom and/or hydrogen atom, such as an alkoxy group.

Examples of alkyl groups in which either a portion of, or all of, the hydrogen atoms have been substituted with a hetero atom include fluorinated lower alkyl groups of 1 to 5 carbon atoms in which either a portion of, or all of, the hydrogen atoms have been substituted with fluorine atoms, groups in which two hydrogen atoms bonded to the same carbon atom have been substituted with a single oxygen atom (namely, groups containing a carbonyl group (C=O)), and groups in which two hydrogen atoms bonded to the same carbon atom have been substituted with a single sulfur atom (namely, groups containing a thiocarbonyl group (C=S)).

Examples of groups in which a portion of the carbon atoms of an alkyl group have been substituted with a hetero atom include examples in which a carbon atom has been substituted with a nitrogen atom (for example, branched or cyclic alkyl groups containing a —$CH_2$— group within the structure, wherein the —$CH_2$— has been substituted with a —NH— group), and examples in which a carbon atom has been substituted with an oxygen atom (for example, branched or cyclic alkyl groups containing a —$CH_2$— group within the structure, wherein the —$CH_2$— has been substituted with a —O— group).

A straight-chain alkyl group represented by $R^1$ preferably contains from 1 to 5 carbon atoms, and specific examples include a methyl group, ethyl group, n-propyl group, n-butyl group, or n-pentyl group, although a methyl group or ethyl group is particularly preferred.

A branched alkyl group represented by $R^1$ preferably contains from 4 to 10 carbon atoms, and even more preferably from 4 to 8 carbon atoms. Specific examples include an isobutyl group, tert-butyl group, isopentyl group, neopentyl group or tert-pentyl group, and a tert-butyl group is particularly preferred.

A cyclic alkyl group represented by $R^1$ preferably contains from 3 to 20 carbon atoms, even more preferably from 4 to 14 carbon atoms, and most preferably from 5 to 12 carbon atoms.

The basic ring structure within the cyclic alkyl group (the basic ring excluding substituent groups) may be either monocyclic or polycyclic, although a polycyclic structure yields particularly superior effects for the present invention and is consequently preferred. Furthermore, the basic ring may be either a hydrocarbon ring formed solely from carbon and hydrogen, or a heterocycle in which a portion of the carbon atoms that constitute a hydrocarbon ring have been substituted with hetero atoms. In the present invention, groups in which the basic ring structure is a hydrocarbon ring are preferred. Examples of the hydrocarbon ring include monocycloalkanes, bicycloalkanes, tricycloalkanes, and tetracycloalkanes. Specific examples include monocycloalkanes such as cyclopentane and cyclohexane, and polycycloalkanes such as adamantane, norbornane, isobornane, tricyclodecane, and tetracyclododecane. Of these, adamantane, norbornane, tricyclodecane and tetracyclododecane are preferred, and adamantane is particularly desirable.

These basic ring structures may either contain a substituent group on the ring, or may contain no substituent groups. Examples of the substituent group include lower alkyl groups, a fluorine atom, fluorinated lower alkyl groups, and an oxygen atom (=O). Examples of the lower alkyl groups include straight-chain or branched alkyl groups of 1 to 5 carbon atoms such as a methyl group or ethyl group. In those cases where the basic ring structure contains a substituent group, the number of substituent groups is preferably within a range from 1 to 3, and is most preferably 1. The expression "contains a substituent group" means that a hydrogen atom bonded to a carbon atom that constitutes part of the basic ring structure has been substituted with a substituent group.

A cyclic alkyl group represented by $R^1$ is a group in which one hydrogen atom has been removed from the above type of basic ring structure. In the $R^1$ group, the carbon atom bonded to the oxygen atom adjacent to the $R^1$ group is preferably one of the carbon atoms that constitute the above type of basic ring structure, and groups in which the carbon atom bonded to the oxygen atom adjacent to the $R^1$ group is a tertiary carbon atom to which a substituent group such as a lower alkyl group is also bonded yield particularly superior effects for the present invention and are consequently preferred.

Examples of acid-dissociable, dissolution-inhibiting groups that contain a cyclic alkyl group as $R^1$ include the groups represented by formulas (p1-1) to (p1-7) shown below. Of these, groups represented by the general formula (p1-1) are preferred.

[Formula 11]

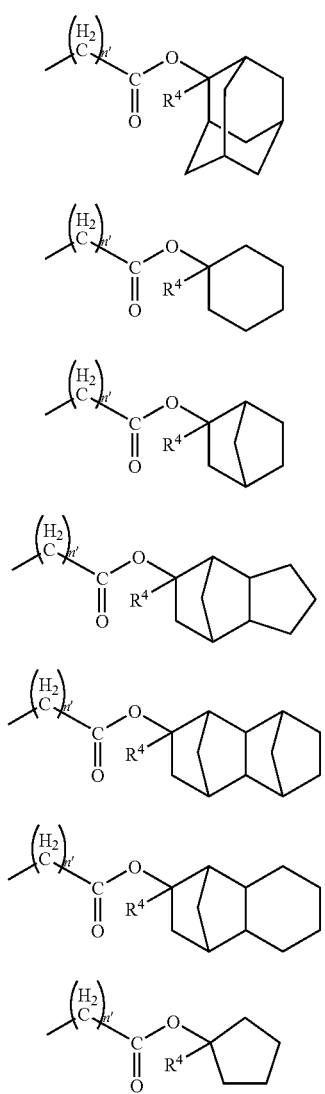

[wherein, $R^4$ represents a lower alkyl group, and n' is as defined above]

The lower alkyl group represented by $R^4$ is an alkyl group of 1 to 5 carbon atoms, and specific examples of suitable groups include straight-chain or branched lower alkyl groups such as a methyl group, ethyl group, propyl group, isopropyl group, n-butyl group, isobutyl group, tert-butyl group, pentyl group, isopentyl group, and neopentyl group. In terms of industrial availability, $R^4$ is preferably a methyl group or ethyl group, and a methyl group is particularly desirable.

$R^1$ is preferably an acid-dissociable, dissolution-inhibiting group that contains a cyclic alkyl group.

In the formula (p2), examples of the $R^2$ group include the same groups as those exemplified above for $R^1$. Of these, $R^2$ is preferably a straight-chain alkyl group or a cyclic alkyl group.

$R^3$ represents a hydrogen atom or a lower alkyl group. A lower alkyl group represented by $R^3$ is an alkyl group of 1 to 5 carbon atoms, and specific examples include straight-chain or branched lower alkyl groups such as a methyl group, ethyl group, propyl group, isopropyl group, n-butyl group, isobutyl group, tert-butyl group, pentyl group, isopentyl group, and neopentyl group. In terms of industrial availability, $R^3$ is preferably a hydrogen atom or a methyl group, and a hydrogen atom is particularly desirable.

Examples of groups represented by the formula (p2) in which $R^2$ is a straight-chain alkyl group include a 1-ethoxyethyl group, 1-ethoxymethyl group, 1-methoxyethyl group, 1-methoxymethyl group, 1-methoxypropyl group, 1-ethoxypropyl group, 1-n-butoxyethyl group, 1-pentafluoroethoxyethyl group, 1-trifluoromethoxyethyl group, and 1-trifluoromethoxymethyl group.

Examples of groups represented by the formula (p2) in which $R^2$ is a cyclic alkyl group include groups represented by the formulas shown below.

[Formula 12]

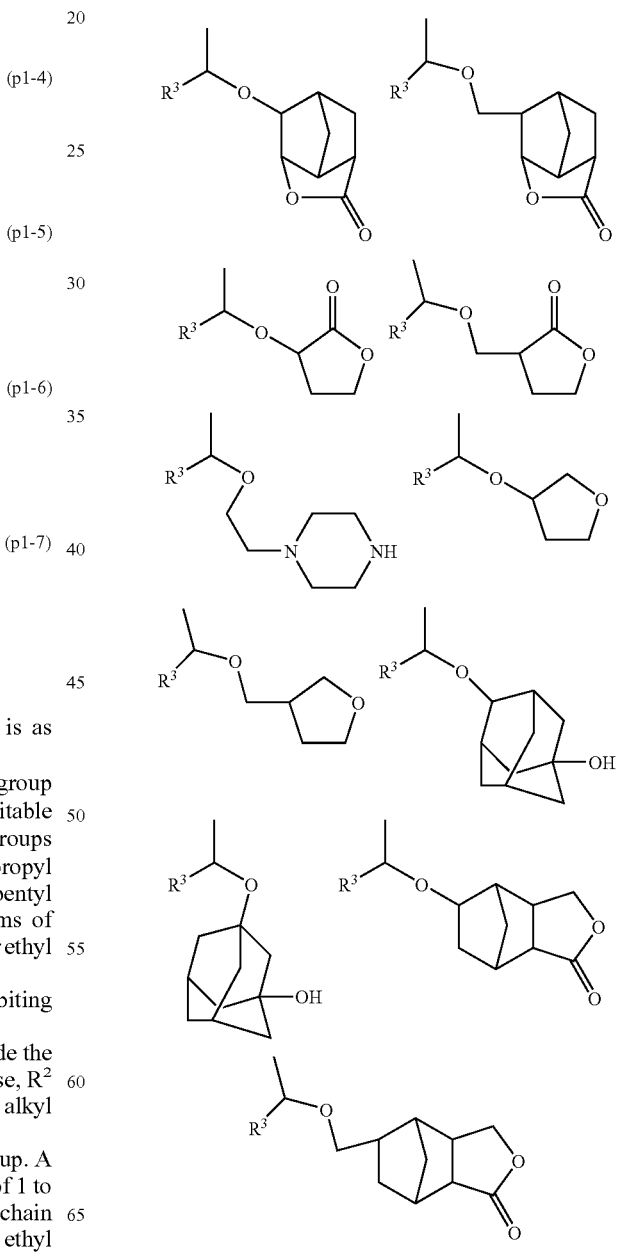

-continued

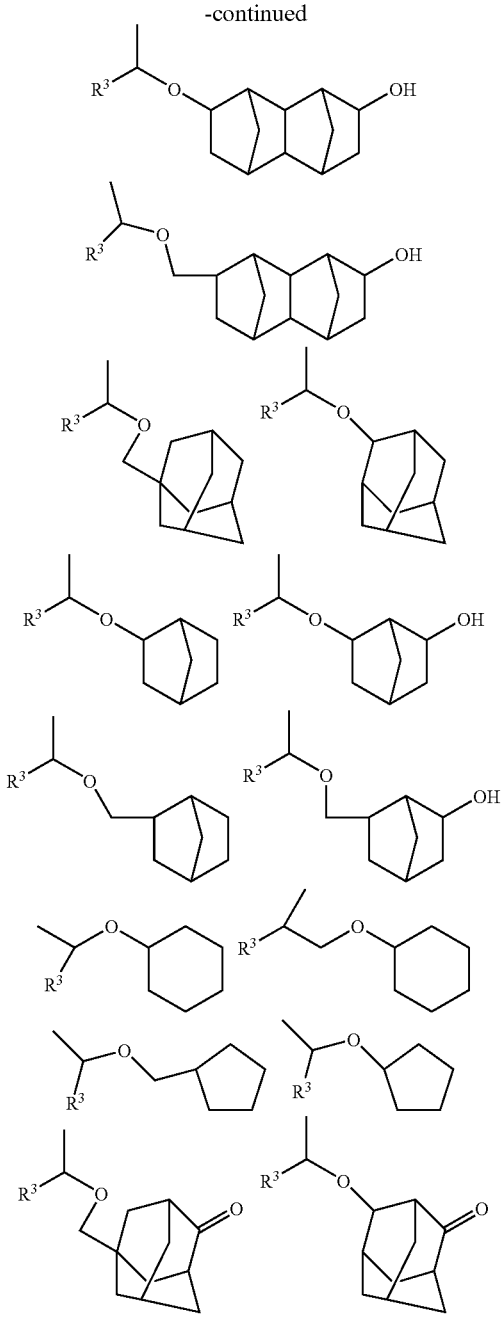

[wherein, R³ represents a hydrogen atom or a lower alkyl group.]

Of these, groups represented by the general formulas (p2-1) and (p2-2) shown below are particularly preferred.

[Formula 13]

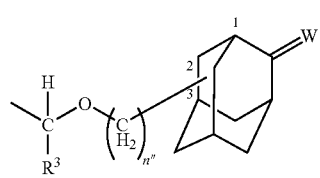

(p2-2)

[wherein, R³ represents a hydrogen atom or a lower alkyl group, n" and m" each represent, independently, an integer from 0 to 2, and W represents either two hydrogen atoms or an oxygen atom]

n" and m" are most preferably either 0 or 1.

There are no particular restrictions on the bonding position between the adamantyl group and the —CHR³—O—(CH₂)$_{n''}$— group, although bonding at either position 1 or position 2 of the adamantyl group is preferred.

In the present invention, the acid-dissociable, dissolution-inhibiting group is preferably a group that contains a cyclic group, such as the groups represented by the above formulas (p1-1) to (p1-7) and (p2-1) to (p2-2), as such groups yield superior effects for the present invention. Compared with those cases where the acid-dissociable, dissolution-inhibiting group is a chain-like group, acid-dissociable, dissolution-inhibiting groups that contain a cyclic group result in lower alkali solubility for the compound (A1). As a result, when the compound (A1) is blended into a positive resist composition, the resistance to alkali developing solutions is increased for the unexposed portions of a resist film formed using the positive resist composition.

In other words, the difference in alkali solubility between the exposed portions and the unexposed portions (the solubility contrast) increases, and the resolution improves.

Furthermore, in the present invention, the properties of the compound (A1) such as the alkali solubility can be adjusted by selection of an appropriate acid-dissociable, dissolution-inhibiting group. In other words, in the compound (A1), when the acid-dissociable, dissolution-inhibiting group is introduced, because the reactivity of the carboxyl groups is higher than that of the hydroxyl groups, the acid-dissociable, dissolution-inhibiting group is introduced at the R' position. As a result, besides the R' portion, the compound structure remains unchanged, meaning that compared with the polymers and the like used as the base material components of conventional positive resist compositions, structural variation between molecules is extremely small. Accordingly, the properties of the entire compound (A1) can be adjusted by selection of an appropriate acid-dissociable, dissolution-inhibiting group. For example, if a comparison is made between cases where a group containing a polycyclic structure such as an adamantane ring is selected as the acid-dissociable, dissolution-inhibiting group, cases where a group containing a monocyclic structure such as a cyclohexane ring is selected, and cases where a group with a chain-like structure is selected, then the alkali solubility of the compound (A1) satisfies the expression: group containing a polycyclic structure<group containing a monocyclic structure<group with a chain-like structure.

Due consideration is preferably given to the structures of the groups R¹¹ to R¹⁷ when selecting the acid-dissociable, dissolution-inhibiting group. This enables the alkali solubility of the compound (A1) to be adjusted to a value within an ideal range for use as a positive resist composition. For example, in those cases where R¹¹ to R¹⁷ are chain-like alkyl groups such as methyl groups, the alkali solubility of the compound (A1) tends to be high, but by selecting a group containing a polycyclic structure such as an adamantane ring as the acid-dissociable, dissolution-inhibiting group, the alkali solubility of the compound (A1) can be reduced. Furthermore, in those cases where $R^{11}$ to $R^{17}$ are cyclic alkyl groups such as cyclohexyl groups or aromatic hydrocarbon groups, the alkali solubility of the compound (A1) tends to be low, but in these cases, by combining these groups with a group containing a monocyclic structure such as a cyclohexane ring as the acid-dissociable, dissolution-inhibiting group, the alkali solubility of the compound (A1) can be increased.

$R^{11}$ to $R^{17}$ each represent, independently, a straight-chain, branched or cyclic alkyl group of 1 to 10 carbon atoms, or an aromatic hydrocarbon group.

The alkyl group is preferably a straight-chain or branched lower alkyl group of 1 to 5 carbon atoms, or a cyclic alkyl group of 5 to 6 carbon atoms. Examples of lower alkyl groups include straight-chain or branched alkyl groups such as a methyl group, ethyl group, propyl group, isopropyl group, n-butyl group, isobutyl group, tert-butyl group, pentyl group, isopentyl group and neopentyl group, and of these, a methyl group is preferred. Examples of cyclic alkyl groups include a cyclohexyl group and cyclopentyl group, and a cyclohexyl group is preferred.

The aromatic hydrocarbon group is preferably a group of 6 to 15 carbon atoms, and examples include a phenyl group, tolyl group, xylyl group, mesityl group, phenethyl group, and naphthyl group.

These alkyl groups or aromatic hydrocarbon groups may include a hetero atom such as an oxygen atom, nitrogen atom or sulfur atom within the group structure.

g and j each represent, independently, an integer of 1 or greater, and k and q each represent, independently, an integer of 0 or greater, provided that g+j+k+q is not greater than 5.

g and j are preferably either 1 or 2, and are most preferably 1.

k is preferably an integer from 0 to 2, is even more preferably either 0 or 1, and is most preferably 1.

q is preferably an integer from 0 to 2, is even more preferably either 0 or 1, and is most preferably 0.

a is an integer from 1 to 3, is preferably either 1 or 2, and is most preferably 1.

b is an integer of 1 or greater, and l and m each represent, independently, an integer of 0 or greater, provided that b+l+m is not greater than 4.

b is preferably either 1 or 2, and is most preferably 1.

l and m are preferably integers from 0 to 2, are even more preferably either 0 or 1, and are most preferably 0.

c represents an integer of 1 or greater, and n and o each represent, independently, an integer of 0 or greater, provided that c+n+o is not greater than 4.

c is preferably either 1 or 2, and is most preferably 1.

n and o are preferably integers from 0 to 2, are even more preferably either 0 or 1, and are most preferably 0.

There are no particular restrictions on the bonding positions of the groups bearing the subscripts b and c (namely, the groups —O—$(CH_2)_a$—CO—OR'), but those compounds in which the —O—$(CH_2)_a$—CO—OR' groups are bonded at least to the para position relative to the group A that is bonded to the benzene rings to which the —O—$(CH_2)_a$—CO—OR' groups are bonded are preferred. These compounds offer certain advantages, including the fact that a low molecular weight compound produced using the compound is ideal for use within a resist composition, and the fact that the compounds are readily synthesized.

There are no particular restrictions on the bonding positions of the hydroxyl groups bearing the subscript g (namely, the groups —$(OH)_g$), although in terms of using the compound to produce a low molecular weight compound that is ideal for use within a resist composition, and ensuring ready synthesis, compounds in which hydroxyl groups are bonded to at least the para position (position 4) of the phenyl groups are preferred.

There are no particular restrictions on the bonding positions of the groups $R^{11}$, $R^{12}$ and $R^{17}$, but in terms of factors such as the ease of synthesis, $R^{11}$ is preferably bonded to at least one of the carbon atoms adjacent to a carbon atom bearing a hydroxyl group.

A represents a group represented by the general formula (Ia) shown above, a group represented by the general formula (Ib) shown above, or an aliphatic cyclic group.

In the formula (Ia), examples of the alkyl groups or aromatic hydrocarbon groups represented by $R^{18}$ and $R^{19}$ include the same groups as the alkyl groups or aromatic hydrocarbon groups exemplified above in relation to $R^{11}$ to $R^{17}$. Of these, from the viewpoint of achieving maximum effect for the present invention, $R^{18}$ and $R^{19}$ are preferably methyl groups. The alkyl groups or aromatic hydrocarbon groups of $R^{11}$ to $R^{17}$ may include a hetero atom such as an oxygen atom, nitrogen atom, or sulfur atom within the group structure.

r, y, and z each represent, independently, either 0 or an integer of 1 or greater, provided that r+y+z is not greater than 4. Of the various possibilities, r is preferably 1, and y+z is preferably 1.

An aliphatic cyclic group represented by A may either contain, or not contain, a substituent group. Examples of the substituent group include lower alkyl groups of 1 to 5 carbon atoms, a fluorine atom, fluorinated lower alkyl groups of 1 to 5 carbon atoms in which a portion of, or all of, the hydrogen atoms have been substituted with fluorine atoms, and an oxygen atom (=O) and the like.

The basic ring structure of the aliphatic cyclic group, excluding any substituent groups, is not restricted to groups formed solely from carbon and hydrogen (hydrocarbon groups), although a hydrocarbon group is preferred. Furthermore, the "hydrocarbon group" may be either saturated or unsaturated, but is typically saturated. A polycyclic group is preferred.

Examples of this type of aliphatic cyclic group include groups in which two or more hydrogen atoms have been removed from a monocycloalkane; and groups in which two or more hydrogen atoms have been removed from a polycycloalkane such as a bicycloalkane, tricycloalkane or tetracycloalkane. Specific examples of these groups include groups in which two or more hydrogen atoms have been removed from a monocycloalkane such as cyclopentane or cyclohexane; and groups in which two or more hydrogen atoms have been removed from or a polycycloalkane such as adamantane, norbornane, isobornane, tricyclodecane or tetracyclododecane. In these groups, either a portion of, or all of, the hydrogen atoms may be substituted with substituent groups (for example, lower alkyl groups, a fluorine atom, or fluoroalkyl groups).

Of these groups, aliphatic cyclic groups of 4 to 15 carbon atoms are preferred, groups in which two hydrogen atoms have been removed from adamantane are even more preferred, and groups in which hydrogen atoms have been removed from position 1 and position 3 of adamantane are particularly desirable.

In terms of ease of synthesis, A is most preferably a group represented by the above general formula (Ib).

As the compound (A1) of the present invention, a compound represented by a general formula (A-2) shown below is preferred, because a compound produced using such a compound is ideal for use within a resist composition.

[Formula 14]

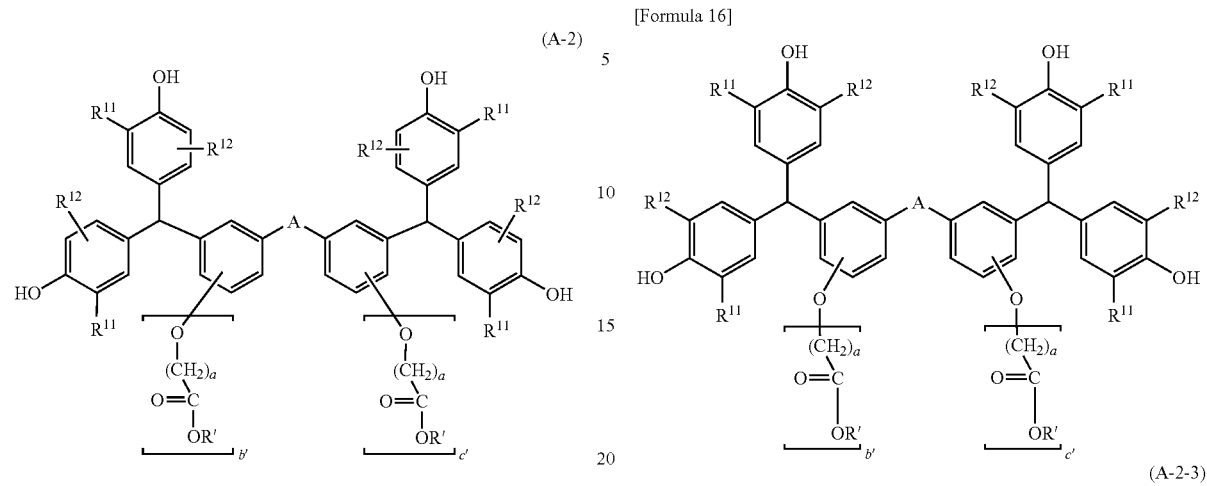

(A-2)

In the formula (A-2), R'R$^{11}$ to R$^{12}$, a and A are as defined for R'R$^{11}$ to R$^{12}$, a and A within the formula (A-1). b' represents an integer from 1 to 4, is preferably either 1 or 2, and is most preferably 1. c' represents an integer from 1 to 4, is preferably either 1 or 2, and is most preferably 1.

Of these compounds, compounds in which b' and c' are both 1 are preferred. Compounds represented by a general formula (A-2-1) shown below are particularly desirable.

[Formula 15]

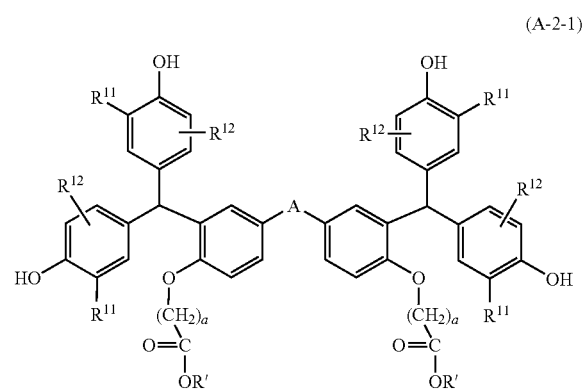

(A-2-1)

[wherein, R'R$^{11}$ to R$^{12}$, a and A are as defined for R'R$^{11}$ to R$^{12}$, a and A within the above general formula (A-1).]

There are no particular restrictions on the bonding position of R$^{12}$, although in terms of ease of synthesis, bonding to the ortho position or meta position relative to the hydroxyl group is preferred.

In other words, as the compound represented by the formula (A-2), compounds represented by general formulas (A-2-2) and (A-2-3) shown below are preferred.

[Formula 16]

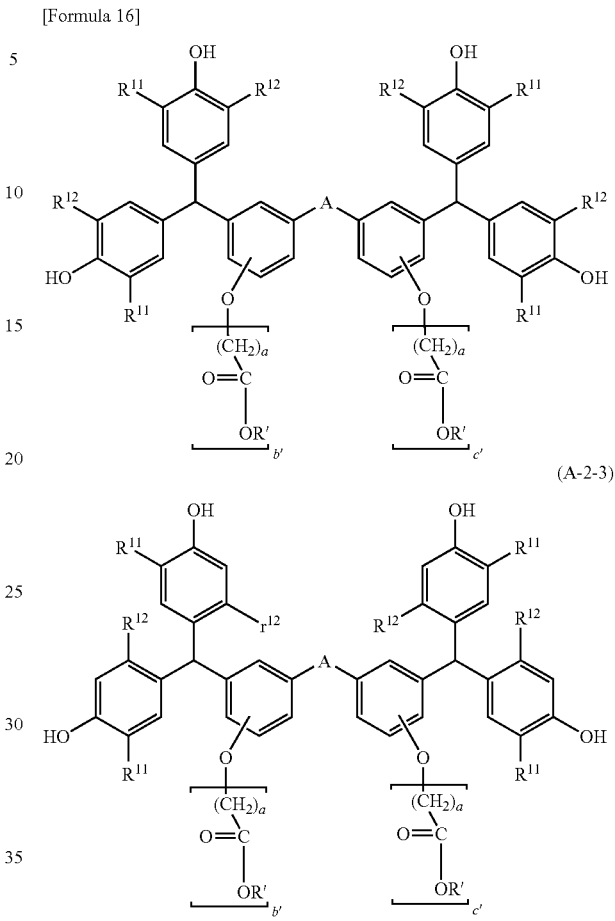

[wherein, R'R$^{11}$ to R$^{12}$, a and A are as defined for R'R$^{11}$ to R$^{12}$, a and A within the above general formula (A-1), and b' and c' are as defined for b' and c' within the above general formula (A-2).]

The compound (A1) is a material that is capable of forming an amorphous (non-crystalline) film using a spin coating method. Here, an amorphous film refers to an optically transparent film that does not crystallize. Spin coating is one of the most commonly used methods for forming thin films.

A judgment as to whether or not the compound is capable of forming an amorphous film using spin coating is determined on the basis of whether or not a film formed by spin coating the compound onto an 8-inch silicon wafer is transparent across the entire film surface. More specifically, judgment can be conducted, for example, in the manner described below. First, the compound is added to a solvent typically used as a resist solvent, such as a mixed solvent of ethyl lactate and propylene glycol monomethyl ether acetate in a ratio (weight ratio) of 40/60 (hereafter this solvent is abbreviated as EM), in sufficient quantity to generate a solution with a concentration of 14% by weight, and dissolution of the compound is achieved by ultrasound treatment (dissolution treatment) using an ultrasonic cleaning apparatus. The resulting solution is spin coated onto a wafer at 1,500 rpm and subjected to optional drying and baking (PAB, Post Applied Bake) at 110° C. for 90 seconds, and a visual judgment is then made as to whether the formed film is transparent, thereby confirming whether or not an amorphous film has been formed. A non-transparent, cloudy film is not an amorphous film.

In the present invention, the compound (A1) preferably generates an amorphous film via the above method that exhibits favorable stability, and for example, compounds for which the amorphous state of the film is retained even after standing for 2 weeks at room temperature following the above PAB treatment are particularly desirable.

The compound (A1) can be produced by using known methods to substitute either a portion of, or all of, the hydrogen atoms at the terminals of the carboxyl groups of a compound (I) represented by a general formula (I) shown below with acid-dissociable, dissolution-inhibiting groups.

[Formula 17]

(I)

[In the formula (I), $R^{11}$ to $R^{17}$, g, j, k, q, a, b, l, m, c, n, o and A are as defined above for $R^{11}$ to $R^{17}$, g, j, k, q, a, b, l, m, c, n, o and A respectively within the above general formula (A-1).]

The compound (I) can be produced by conventional methods, for example by subjecting a bis-salicylaldehyde derivative, in which two salicylaldehydes (which may contain substituent groups) are bonded together via the aforementioned group A, and a phenol compound containing a substituent group to a dehydration condensation under acidic conditions, thereby generating a tris(hydroxyphenyl)methane derivative, and then introducing carboxyalkyloxy groups by reacting a halogenated carboxylic acid such as a bromoacetate derivative with the hydroxyl groups of the tris(hydroxyphenyl) methane derivative. However, in this type of conventional method, controlling the hydroxyl group positions where the carboxyalkyloxy groups are introduced and the number of carboxyalkyloxy groups is difficult, and the yield tends to be low for the compound (I) in which carboxyalkyloxy groups are bonded to both of the two benzene rings linked via the group A.

As a result, the compound (I) is preferably produced using a production method that includes:

a step of reacting a compound (I-1) represented by a general formula (I-1) shown below and a compound (I-2) represented by a general formula (I-2) shown below to obtain a compound (I-3) represented by a general formula (I-3) shown below (hereafter referred to as the compound (I-3) formation step), and a step of obtaining the compound (I) (hereafter referred to as the compound (I) formation step) via a step of reacting the compound (I-3) and a compound (I-4) represented by a general formula (I-4) shown below under acidic conditions.

[Formula 18]

(I-1)

(I-2)

(I-3)

(I-4)

[wherein, X represents a halogen atom; R represents a protective group, and $R^{11}$ to $R^{17}$, g, j, k, q, a, b, l, m, c, n, o and A are as defined above for $R^{11}$ to $R^{17}$, g, j, k, q, a, b, l, m, c, n, o and A respectively within the above general formula (I).]

<Compound (I-3) Formation Step>

In the formulas (I-1) to (I-3), $R^{13}$ to $R^{16}$, a, b, l, m, c, n, o and A are as defined above for $R^{13}$ to $R^{16}$, a, b, l, m, c, n, o and A respectively within the above general formula (I).

In the general formula (I-2), examples of the halogen atom represented by X include a bromine atom, chlorine atom, and fluorine atom. A bromine atom is preferred as it offers superior reactivity.

There are no particular restrictions on the protective group represented by R, provided it is an acid-dissociable group that does not react during the reaction between the compound (I-1) and the compound (I-2), but then dissociates under the acidic conditions used during reaction of the compound (I-3) in the subsequent compound (I) formation step, and this group may selected from the many groups typically proposed as protective groups.

Examples of such protective groups include the same groups as those exemplified above for the acid-dissociable, dissolution-inhibiting group of R' within the above formula (A-1).

In terms of factors such as ensuring favorable acid dissociability and ease of availability, tertiary alkyl groups or alkoxyalkyl groups are preferred, chain-like groups (such as chain-like tertiary alkyl groups; and alkoxyalkyl groups of the aforementioned general formula (p2) in which $R^2$ represents a straight-chain or branched alkyl group, which may include a hetero atom within the structure, and $R^3$ represents a hydrogen atom or a straight-chain or branched lower alkyl group) are particularly preferred, chain-like tertiary alkyl groups are even more preferred, and a tert-butyl group is the most desirable.

The compound (I-1) and the compound (I-2) can be reacted using conventional methods, for example by dissolving the compound (I-1) in an organic solvent such as acetone, adding a base such as potassium carbonate to the solution, and then adding the compound (I-2) to the stirred solution of the compound (I-1), in a quantity that provides approximately 2 molar equivalents of the compound (I-2) relative to the compound (I-1).

The organic solvent used during this reaction may be any solvent capable of dissolving the compound (I-1), the compound (I-2) and the produced compound (I-3), and may be selected appropriately from typical organic solvents. Examples of these typical organic solvents include ketones such as acetone, methyl ethyl ketone, methyl amyl ketone, and cyclohexanone; ethers such as tetrahydrofuran (THF), dioxane, glyme, and propylene glycol monomethyl ether; esters such as ethyl acetate and ethyl lactate; ether esters such as propylene glycol methyl ether acetate; and lactones such as γ-butyrolactone. These solvents may be used either alone or as mixtures.

The reaction temperature is preferably within a range from 10 to 60° C., even more preferably from 20 to 60° C., and can usually be set to room temperature (20 to 25° C.).

The reaction time is preferably within a range from 1 to 24 hours, and is even more preferably from 4 to 15 hours.

Following completion of the reaction, the reaction solution may be used, as is, in the following step, or water/ethyl acetate or the like may be added, and the organic phase (the phase containing the ethyl acetate or the like) then concentrated under reduced pressure to obtain the compound (I-3).

<Compound (I) Formation Step>

In the general formula (I-4), $R^{11}$, $R^{12}$, $R^{17}$, g, j, k and q are as defined above for $R^{11}$, $R^{12}$, $R^{17}$, g, j, k and q respectively within the above general formula (I).

In this step, a step is first conducted for reacting the compound (I-3) and the compound (I-4) under acidic conditions. This step results in a reaction between the formyl groups (—CHO) of the compound (I-3) and the compound (I-4), as well as the dissociation of the protective groups R from the compound (I-3), thereby forming carboxyl groups.

Specifically, reaction can be conducted, for example, by dissolving approximately 4 molar equivalents of the compound (I-4) relative to the compound (I-3) being used within an organic solvent such as methanol, adding an acid such as hydrochloric acid to the solution, and then adding the compound (I-3).

There are no particular restrictions on the acid used during this step, provided the compound (I-3) and the compound (I-4) undergo reaction and the protective groups R dissociate. Examples of preferred acids include hydrochloric acid, sulfuric acid, sulfuric anhydride, p-toluenesulfonic acid, methanesulfonic acid, trifluoromethanesulfonic acid, oxalic acid, formic acid, phosphoric acid, trichloroacetic acid, and trifluoroacetic acid. Hydrochloric acid is particularly favorable.

These acids may be used either alone, or in mixtures of two or more different acids.

The quantity of acid added, for example in the case of a 35% by weight aqueous solution of hydrochloric acid, is typically within a range from 1 to 700 parts by weight, and is preferably from 100 to 600 parts by weight, per 100 parts by weight of the compound (I-3).

The reaction temperature is preferably within a range from 20 to 80° C., and is even more preferably from 30 to 65° C.

The reaction time is preferably within a range from 2 to 96 hours, and is even more preferably from 5 to 72 hours.

Following completion of the reaction, a base such as sodium hydroxide is added to the reaction solution to neutralize the acid within the reaction solution. At this time, in those cases where an alcohol such as methanol was used as the organic solvent for the reaction solution, the produced carboxyl groups may have undergone slight esterification by the alcohol. As a result, in order to hydrolyze such esters, the addition of an excess of base is preferred.

In the thus obtained reaction solution, the compound (I) is dissolved in the form of a salt. Accordingly, if the reaction solution is transferred to a separating funnel, washed with water/diethyl ether or the like to remove any raw materials (such as the compounds used in the reaction), and the water phase is then extracted and neutralized with an aqueous solution of hydrochloric acid, a precipitate develops. The compound (I) can be obtained by recovering this precipitate by filtration or the like.

This unpurified compound (I) may be subjected to a purification treatment such as re-precipitation.

As described below, the above compound (A1) can be used favorably as a base material component (A) within a positive resist composition that includes the base material component (A), which exhibits increased alkali solubility under the action of acid, and an acid generator component (B) that generates acid upon irradiation.

By using a positive resist composition containing the compound (A1), a high resolution resist pattern such as an ultra fine resist pattern with pattern dimensions of 200 nm or less can be formed, and the roughness can also be reduced.

It is thought that this effect is due to the uniformity of the compound (A1). In other words, in conventional resists that use a high molecular weight polymer (resin) as the base material component of the resist material, controlling the molecular weight dispersion and the alkali solubility dispersion is very difficult. As a result, there is a limit to the degree of reduction that can be achieved in the LER, which is caused by factors such as these dispersions, and the molecular weight itself.

Furthermore, in the case of conventional low molecular weight compounds (low molecular weight materials) that have been proposed to counter the above problems, as described in the above non-patent references 1 and 2, because alkali-soluble groups are protected with acid-dissociable, dissolution-inhibiting groups, variations occur between individual molecules in terms of the positions of the protected alkali-soluble groups and the protection ratio, and as a result, variations also develop in the properties of the compound, causing similar problems to those outlined above.

In contrast, the compound (A1) is a low molecular weight non-polymer. Furthermore, as described above, the compound (I) used in producing the compound (A1) contains phenolic hydroxyl groups and carboxyl groups as alkali-soluble groups, meaning that when the alkali-soluble groups are protected with acid-dissociable, dissolution-inhibiting groups, the more reactive carboxyl groups undergo selective protection. As a result, the resulting compound (A1) exhibits less variation in structure and molecular weight than a compound containing an equivalent quantity of solely hydroxyl groups as the alkali-soluble groups. As result, the compound (A1) exhibits minimal variation between molecules in terms of properties such as the alkali solubility, the hydrophilicity and the hydrophobicity, meaning a resist film with uniform properties can be formed. Accordingly, it is surmised that by using the compound (A1), a resist film with uniform properties can be formed, and that as a result, a high resolution resist pattern can be formed, and the level of roughness can also be reduced.

Moreover, as described above, because the compound (A1) exhibits uniform properties, and is thought to enable the formation of a resist film of uniform properties (such as alkali solubility, the hydrophilicity and the hydrophobicity), use of the compound (A1) also enables a reduction in the level of defects. Here, the term "defects" refers to general abnormalities detected by inspection of the resist pattern following developing, from directly above the resist pattern, using a surface defect inspection device such as that manufactured by KLA Tencor Corporation (brand name: KLA). Examples of these abnormalities include post-developing scum, foam, dust, bridges across different portions of the resist pattern, color irregularities, and precipitated deposits.

Furthermore, because the compound (A1) exhibits uniform properties, and is thought to display uniform solubility in organic solvents and the like, the storage stability of a positive resist composition containing the compound (A1) also improves.

Positive Resist Composition of Second Embodiment

A positive resist composition of a second embodiment of the present invention includes a base material component (A) that exhibits increased alkali solubility under the action of acid (hereafter referred to as the component (A)), and an acid generator component (B) that generates acid upon irradiation (hereafter referred to as the component (B)), wherein the component (A) includes the compound (A1).

In the positive resist composition including the component (A) and the component (B), when an acid generated from the component (B) upon exposure acts upon the component (A), the entire component (A) changes from an alkali-insoluble state to an alkali-soluble state. As a result, when a resist film formed from the positive resist composition is selectively exposed during the formation of a resist pattern, or alternatively is exposed and then subjected to post exposure baking, the exposed portions of the resist shift to an alkali-soluble state, whereas the unexposed portions remain insoluble in alkali, meaning alkali developing can then be used to form a positive resist pattern.

[Component (A)]

The component (A) includes the compound (A1).

The compound (A1) may use either a single compound, or a combination of two or more different compounds.

The proportion of the compound (A1) within the component (A) is preferably greater than 40% by weight, even more preferably greater than 50% by weight, even more preferably greater than 80% by weight, and is most preferably 100% by weight.

The proportion of the compound (A1) within the component (A) can be measured using a technique such as reverse-phase chromatography.

The component (A) may also include any of the conventional resin components that have been proposed as base material components for chemically amplified resists (hereafter also referred to as the component (A2)), provided the inclusion of these components does not impair the effects obtained by using the compound (A1).

Examples of the component (A2) include any of the materials proposed as base resins for conventional chemically amplified positive resist compositions for use with a KxF excimer laser or positive resist compositions for use with an ArF excimer laser, and these can be selected in accordance with the nature of the exposure light source used during resist pattern formation.

The quantity of the component (A) within the positive resist composition may be adjusted in accordance with the film thickness of the resist to be formed.

[Component (B)]

There are no particular restrictions on the component (B), which can use any of the acid generators proposed for use within conventional chemically amplified resists.

Examples of these acid generators are numerous, and include onium salt-based acid generators such as iodonium salts and sulfonium salts, oxime sulfonate-based acid generators, diazomethane-based acid generators such as bisalkyl or bisaryl sulfonyl diazomethanes and poly(bis-sulfonyl)diazomethanes, nitrobenzyl sulfonate-based acid generators, iminosulfonate-based acid generators, and disulfone-based acid generators.

Examples of onium salt-based acid generators include acid generators represented by a general formula (b-0) shown below.

[Formula 19]

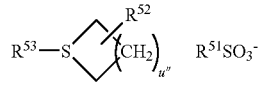

(b-0)

[wherein, $R^{51}$ represents a straight-chain, branched-chain or cyclic alkyl group, or a straight-chain, branched-chain or cyclic fluoroalkyl group; $R^{52}$ represents a hydrogen atom, hydroxyl group, halogen atom, straight-chain, branched-chain or cyclic alkyl group, straight-chain or branched-chain haloalkyl group, or a straight-chain or branched-chain alkoxy group; $R^{53}$ represents an aryl group that may contain a substituent group; and u" represents an integer from 1 to 3.]

In the general formula (b-0), $R^{51}$ represents a straight-chain, branched-chain or cyclic alkyl group, or a straight-chain, branched-chain or cyclic fluoroalkyl group.

The straight-chain or branched-chain alkyl group preferably contains from 1 to 10 carbon atoms, even more from preferably 1 to 8 carbon atoms, and most preferably from 1 to 4 carbon atoms.

The cyclic alkyl group preferably contains from 4 to 12 carbon atoms, even more preferably from 5 to 10 carbon atoms, and most preferably from 6 to 10 carbon atoms.

The fluoroalkyl group preferably contains from 1 to 10 carbon atoms, even more preferably from 1 to 8 carbon atoms, and most preferably from 1 to 4 carbon atoms. Furthermore, the fluorination ratio of the fluoroalkyl group (the ratio of the number of substituted fluorine atoms relative to the total number of hydrogen atoms within the alkyl group) is preferably within a range from 10 to 100%, and even more preferably from 50 to 100%, and groups in which all of the hydrogen atoms have been substituted with fluorine atoms yield the strongest acids, and are consequently the most desirable.

As the group $R^{51}$, a straight-chain alkyl group or a straight-chain fluoroalkyl group is the most desirable.

$R^{52}$ represents a hydrogen atom, a hydroxyl group, a halogen atom, a straight-chain, branched-chain or cyclic alkyl group, a straight-chain or branched-chain haloalkyl group, or a straight-chain or branched-chain alkoxy group.

Examples of the halogen atom represented by $R^{52}$ include a fluorine atom, bromine atom, chlorine atom or iodine atom, and a fluorine atom is preferred.

A straight-chain or branched-chain alkyl group represented by $R^{52}$ preferably contains from 1 to 5 carbon atoms, even more preferably from 1 to 4 carbon atoms, and most preferably from 1 to 3 carbon atoms.

A cyclic alkyl group represented by $R^{52}$ preferably contains from 4 to 12 carbon atoms, even more preferably from 4 to 10 carbon atoms, and most preferably from 5 to 10 carbon atoms.

Examples of the haloalkyl group represented by $R^{52}$ include groups in which either a portion of, or all of, the hydrogen atoms within the alkyl group have been substituted with halogen atoms. Here, an alkyl group refers to the same type of group as the "straight-chain or branched-chain alkyl group" described above for the group $R^{52}$. Examples of the substituent halogen atom include the same halogen atoms as those described above in relation to the "halogen atom" for the group $R^{52}$. In the haloalkyl group, 50 to 100% of the total number of hydrogen atoms are preferably substituted with halogen atoms, and groups in which all of the hydrogen atoms have been substituted are particularly desirable.

Examples of the alkoxy group represented by $R^{52}$ include straight-chain and branched-chain groups in which the number of carbon atoms is preferably within a range from 1 to 5, even more preferably from 1 to 4, and most preferably from 1 to 3.

Of the groups described above, $R^{52}$ is most preferably a hydrogen atom.

$R^{53}$ represents an aryl group that may contain a substituent group, and examples of the basic ring structure excluding any substituent groups (the matrix structure) include a naphthyl group, phenyl group or anthracenyl group, and from the viewpoints of maximizing the effects of the present invention and ensuring favorable absorption of the exposure light such as the ArF excimer laser light, a phenyl group is preferred.

Examples of the substituent group include a hydroxyl group or a lower alkyl group (which may be a straight-chain or branched-chain group, preferably contains not more than 5 carbon atoms, and is most preferably a methyl group).

The aryl group represented by $R^{53}$ preferably contains no substituent groups.

u" represents an integer from 1 to 3, is preferably either 2 or 3, and is most preferably 3.

Examples of preferred acid generators represented by the general formula (b-0) include compounds represented by the chemical formulas shown below.

[Formula 20]

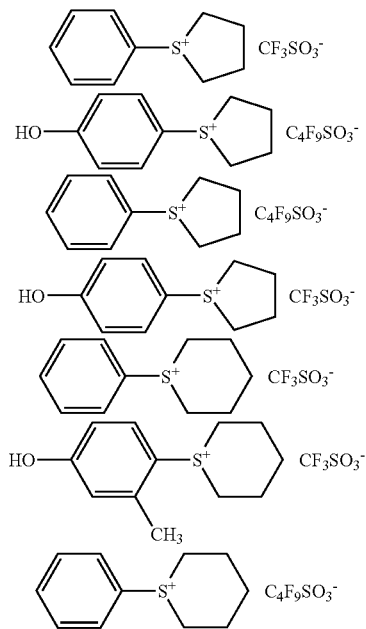

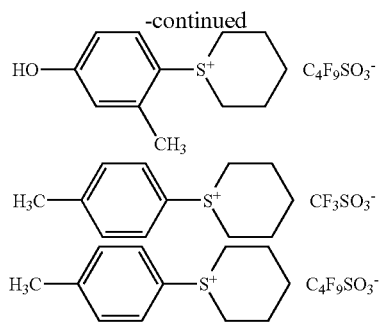

The acid generator represented by the general formula (b-0) may use either a single compound, or a mixture of two or more different compounds.

Furthermore, examples of onium salt-based acid generators besides those represented by the above general formula (b-0) include compounds represented by general formulas (b-1) and (b-2) shown below.

[Formula 21]

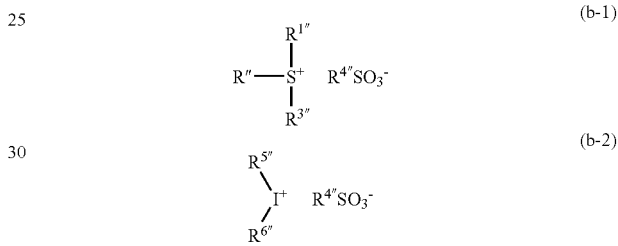

[wherein, $R^{1"}$ to $R^{3"}$, and $R^{5"}$ to $R^{6"}$ each represent, independently, an aryl group or an alkyl group; and $R^{4"}$ represents a straight-chain, branched or cyclic alkyl group or fluoroalkyl group; provided that at least one of $R^{1"}$ to $R^{3"}$ represents an aryl group, and at least one of $R^{5"}$ to $R^{6"}$ represents an aryl group]

In the formula (b-1), $R^{1"}$ to $R^{3"}$ each represent, independently, an aryl group or an alkyl group. Of the groups $R^{1"}$ to $R^{3"}$, at least one group represents an aryl group. Compounds in which at least two of $R^{1"}$ to $R^{3"}$ represent aryl groups are preferred, and compounds in which all of $R^{1"}$ to $R^{3"}$ are aryl groups are the most desirable.

There are no particular restrictions on the aryl groups of $R^{1"}$ to $R^{3"}$, and suitable examples include aryl groups of 6 to 20 carbon atoms, in which either a portion of, or all of, the hydrogen atoms of these aryl groups may be either substituted, or not substituted, with alkyl groups, alkoxy groups, or halogen atoms and the like. In terms of enabling low-cost synthesis, aryl groups of 6 to 10 carbon atoms are preferred. Specific examples of such groups include a phenyl group and a naphthyl group.

Alkyl groups that may be used for substitution of the hydrogen atoms of the above aryl groups are preferably alkyl groups of 1 to 5 carbon atoms, and a methyl group, ethyl group, propyl group, n-butyl group or tert-butyl group is the most desirable.

Alkoxy groups that may be used for substitution of the hydrogen atoms of the above aryl groups are preferably alkoxy groups of 1 to 5 carbon atoms, and a methoxy group or ethoxy group is the most desirable.

Halogen atoms that may be used for substitution of the hydrogen atoms of the above aryl groups are preferably fluorine atoms.

There are no particular restrictions on the alkyl groups of $R^{1\prime\prime}$ to $R^{3\prime\prime}$, and suitable examples include straight-chain, branched, or cyclic alkyl groups of 1 to 10 carbon atoms. From the viewpoint of achieving excellent resolution, alkyl groups of 1 to 5 carbon atoms are preferred. Specific examples include a methyl group, ethyl group, n-propyl group, isopropyl group, n-butyl group, isobutyl group, n-pentyl group, cyclopentyl group, hexyl group, cyclohexyl group, nonyl group, and decanyl group. In terms of achieving superior resolution and enabling low-cost synthesis, a methyl group is the most desirable.

Of the above possibilities, compounds in which $R^{1\prime\prime}$ to $R^{3\prime\prime}$ are all phenyl groups are the most preferred.

The group $R^{4\prime\prime}$ represents a straight-chain, branched or cyclic alkyl group or fluoroalkyl group. The straight-chain or branched alkyl group preferably contains from 1 to 10 carbon atoms, even more preferably from 1 to 8 carbon atoms, and most preferably from 1 to 4 carbon atoms.

Suitable cyclic alkyl groups include the same groups as those exemplified above in relation to the group $R^{1\prime\prime}$, and cyclic groups of 4 to 15 carbon atoms are preferred, groups of 4 to 10 carbon atoms are even more preferred, and groups of 6 to 10 carbon atoms are the most desirable.

As the above fluoroalkyl group, groups of 1 to 10 carbon atoms are preferred, groups of 1 to 8 carbon atoms are even more preferred, and groups of 1 to 4 carbon atoms are the most desirable. Furthermore, the fluorination ratio of the fluoroalkyl group (namely, the fluorine atom proportion within the alkyl group) is preferably within a range from 10 to 100%, and even more preferably from 50 to 100%, and groups in which all of the hydrogen atoms have been substituted with fluorine atoms yield the strongest acids, and are consequently the most desirable.

The group $R^{4\prime\prime}$ is most preferably a straight-chain or cyclic alkyl group, or a fluoroalkyl group.

In the formula (b-2), $R^{5\prime\prime}$ to $R^{6\prime\prime}$ each represent, independently, an aryl group or an alkyl group. At least one of $R^{5\prime\prime}$ to $R^{6\prime\prime}$ represents an aryl group. Compounds in which both $R^{5\prime\prime}$ and $R^{6\prime\prime}$ are aryl groups are the most preferred.

Suitable examples of the aryl groups of the groups $R^{5\prime\prime}$ to $R^{6\prime\prime}$ include the same aryl groups as those described above for the groups $R^{1\prime\prime}$ to $R^{3\prime\prime}$.

Suitable examples of the alkyl groups of the groups $R^{5\prime\prime}$ to $R^{6\prime\prime}$ include the same alkyl groups as those described above for the groups $R^{1\prime\prime}$ to $R^{3\prime\prime}$.

Of the above possibilities, compounds in which $R^{5\prime\prime}$ and $R^{6\prime\prime}$ are both phenyl groups are the most preferred.

Suitable examples of the group $R^{4\prime\prime}$ in the formula (b-2) include the same groups as those described for the group $R^{4\prime\prime}$ in the aforementioned formula (b-1).

Specific examples of onium salt-based acid generators represented by the general formula (b-1) or (b-2) include diphenyl)iodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl)diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, and diphenyl(1-(4-methoxy)naphthyl)sulfonium trifluoromethanesulfonate, heptafluoropropanesulfonate or nonafluorobutanesulfonate. Furthermore, onium salts in which the anion portion of the above onium salts have been substituted with methanesulfonate, n-propanesulfonate, n-butanesulfonate, or n-octanesulfonate can also be used.

Furthermore, onium salt-based acid generators in which the anion portion within one of the above general formulas (b-1) or (b-2) has been substituted with an anion portion represented by a general formula (b-3) or (b-4) shown below (and in which the cation portion is the same as that shown in (b-1) or (b-2)) can also be used.

[Formula 22]

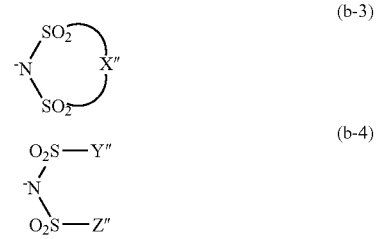

[wherein, X" represents an alkylene group of 2 to 6 carbon atoms in which at least one hydrogen atom has been substituted with a fluorine atom; and Y" and Z" each represent, independently, an alkyl group of 1 to 10 carbon atoms in which at least one hydrogen atom has been substituted with a fluorine atom]

The group X" is a straight-chain or branched alkylene group in which at least one hydrogen atom has been substituted with a fluorine atom, and the number of carbon atoms within the alkylene group is typically within a range from 2 to 6, preferably from 3 to 5, and is most preferably 3.

Y" and Z" each represent, independently, a straight-chain or branched alkyl group in which at least one hydrogen atom has been substituted with a fluorine atom, and the number of carbon atoms within the alkyl group is typically within a range from 1 to 10, preferably from 1 to 7, and is most preferably from 1 to 3.

Within the above ranges for the numbers of carbon atoms, lower numbers of carbon atoms within the alkylene group X" or the alkyl groups Y" and Z" are preferred for reasons including better solubility within the resist solvent.

Furthermore, in the alkylene group X" or the alkyl groups Y" and Z", the larger the number of hydrogen atoms that have been substituted with fluorine atoms, the stronger the acid becomes, and the transparency relative to high energy light beams with a wavelength of 200 nm or less or electron beams also improves favorably. The fluorine atom proportion within the alkylene group or alkyl groups, namely the fluorination ratio, is preferably within a range from 70 to 100%, and even more preferably from 90 to 100%, and perfluoroalkylene or perfluoroalkyl groups in which all of the hydrogen atoms have been substituted with fluorine atoms are the most desirable.

In the present invention, the term "oxime sulfonate-based acid generator" describes a compound that contains at least one group represented by a general formula (B-1) shown below, and generates acid upon irradiation. These types of oxime sulfonate-based acid generators are widely used within chemically amplified resist compositions, and any of these conventional compounds can be used.

[Formula 23]

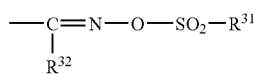

(B-1)

(In the formula (B-1), $R^{31}$ and $R^{32}$ each represent, independently, an organic group.)

The organic groups of $R^{31}$ and $R^{32}$ are groups that include a carbon atom, and may also include atoms other than carbon atoms (such as a hydrogen atom, oxygen atom, nitrogen atom, sulfur atom, or halogen atom (such as a fluorine atom or chlorine atom)).

The organic group of $R^{31}$ is preferably a straight-chain, branched or cyclic alkyl group or aryl group. These alkyl groups or aryl groups may also include a substituent group. There are no particular restrictions on such substituent groups, and suitable examples include a fluorine atom or a straight-chain, branched or cyclic alkyl group of 1 to 6 carbon atoms. Here, the expression "include a substituent group" means that either a portion of, or all of, the hydrogen atoms of the alkyl group or aryl group are substituted with substituent groups.

The alkyl group preferably contains from 1 to 20 carbon atoms, even more preferably from 1 to 10 carbon atoms, even more preferably from 1 to 8 carbon atoms, even more preferably from 1 to 6 carbon atoms, and most preferably from 1 to 4 carbon atoms. Furthermore, alkyl groups that are partially or completely halogenated (hereafter also referred to as haloalkyl groups) are preferred. A partially halogenated alkyl group is an alkyl group in which a portion of the hydrogen atoms have been substituted with halogen atoms, whereas a completely halogenated alkyl group is an alkyl group in which all of the hydrogen atoms have been substituted with halogen atoms. Examples of the halogen atoms include a fluorine atom, chlorine atom, bromine atom or iodine atom, although a fluorine atom is particularly desirable. In other words, the haloalkyl group is preferably a fluoroalkyl group.

The aryl group preferably contains from 4 to 20 carbon atoms, even more preferably from 4 to 10 carbon atoms, and most preferably from 6 to 10 carbon atoms. Aryl groups that are partially or completely halogenated are preferred. A partially halogenated aryl group is an aryl group in which a portion of the hydrogen atoms have been substituted with halogen atoms, whereas a completely halogenated aryl group is an aryl group in which all of the hydrogen atoms have been substituted with halogen atoms.

As the group $R^{31}$, an alkyl group of 1 to 4 carbon atoms containing no substituent groups, or a fluoroalkyl group of 1 to 4 carbon atoms is the most desirable.

The organic group of $R^{32}$ is preferably a straight-chain, branched or cyclic alkyl group or aryl group, or a cyano group. Examples of suitable alkyl groups and aryl groups for $R^{32}$ include the same alkyl groups and aryl groups described above in relation to $R^{31}$.

As the group $R^{32}$, a cyano group, an alkyl group of 1 to 8 carbon atoms containing no substituent groups, or a fluoroalkyl group of 1 to 8 carbon atoms is the most desirable.

Particularly preferred oxime sulfonate-based acid generators include the compounds represented by general formulas (B-2) and (B-3) shown below.

[Formula 24]

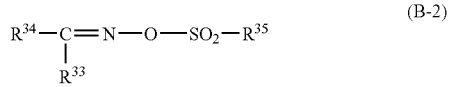

(B-2)

[In the formula (B-2), $R^{33}$ represents a cyano group, an alkyl group containing no substituent groups, or a haloalkyl group. $R^{34}$ represents an aryl group. $R^{35}$ represents an alkyl group containing no substituent groups, or a haloalkyl group.]

[Formula 25]

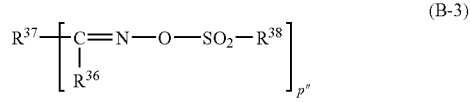

(B-3)

[In the formula (B-3), $R^{36}$ represents a cyano group, an alkyl group containing no substituent groups, or a haloalkyl group. $R^{37}$ represents a bivalent or trivalent aromatic hydrocarbon group. $R^{38}$ represents an alkyl group containing no substituent groups, or a haloalkyl group. p" is either 2 or 3.]

In the above general formula (B-2), the alkyl group containing no substituent groups or haloalkyl group represented by $R^{33}$ preferably contains from 1 to 10 carbon atoms, even more preferably from 1 to 8 carbon atoms, and most preferably from 1 to 6 carbon atoms.

The group $R^{33}$ is preferably a haloalkyl group, and is even more preferably a fluoroalkyl group.

In a fluoroalkyl group represented by $R^{33}$, at least 50% of the hydrogen atoms of the alkyl group are preferably fluorinated, and this ratio is even more preferably 70% or higher, and is most preferably 90% or higher.

The aryl group represented by $R^{34}$ is preferably a group in which one hydrogen atom has been removed from an aromatic hydrocarbon ring, such as a phenyl group, biphenyl group, fluorenyl group, naphthyl group, anthracyl group or phenanthryl group, or a heteroaryl group in which a portion of the carbon atoms that constitute the ring structure within one of the above groups have been substituted with a hetero atom such as an oxygen atom, sulfur atom or nitrogen atom. Of these possibilities, a fluorenyl group is particularly preferred.

The aryl group of $R^{34}$ may include a substituent group such as an alkyl group, haloalkyl group or alkoxy group of 1 to 10 carbon atoms. The alkyl group or haloalkyl group substituent groups preferably contain from 1 to 8 carbon atoms, and even more preferably from 1 to 4 carbon atoms. Furthermore, the haloalkyl group is preferably a fluoroalkyl group.

The alkyl group containing no substituent groups or haloalkyl group represented by $R^{35}$ preferably contains from 1 to 10 carbon atoms, even more preferably from 1 to 8 carbon atoms, and most preferably from 1 to 6 carbon atoms.

The group $R^{35}$ is preferably a haloalkyl group, and is even more preferably a partially or completely fluorinated alkyl group.

In the fluoroalkyl group of $R^{35}$, at least 50% of the hydrogen atoms of the alkyl group are preferably fluorinated, and groups in which 70% or more, and even more preferably 90% or more, of the hydrogen atoms are fluorinated are particularly desirable as they increase the strength of the acid that is generated. Completely fluorinated alkyl groups in which 100% of the hydrogen atoms have been substituted with fluorine atoms are the most desirable.

In the above general formula (B-3), examples of the alkyl group containing no substituent groups or haloalkyl group represented by $R^{36}$ include the same alkyl groups containing no substituent groups and haloalkyl groups described above for the group $R^{33}$.

Examples of the bivalent or trivalent aromatic hydrocarbon group represented by $R^{37}$ include groups in which a further one or two hydrogen atoms respectively are removed from an aryl group of the aforementioned group $R^{34}$.

Examples of the alkyl group containing no substituent groups or haloalkyl group represented by $R^{38}$ include the same alkyl groups containing no substituent groups and haloalkyl groups described above for the group $R^{35}$.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)-benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Furthermore, the oxime sulfonate-based acid generators disclosed in Japanese Unexamined Patent Application, First Publication No. Hei 9-208554 ([formula 18] to [formula 19] shown in paragraphs [0012] to [0014]), and the oxime sulfonate-based acid generators disclosed in WO2004/074242A2 (Examples 1 to 40 on pages 65 to 85) can also be used favorably.

Furthermore, preferred compounds include those shown below.

[Formula 26]

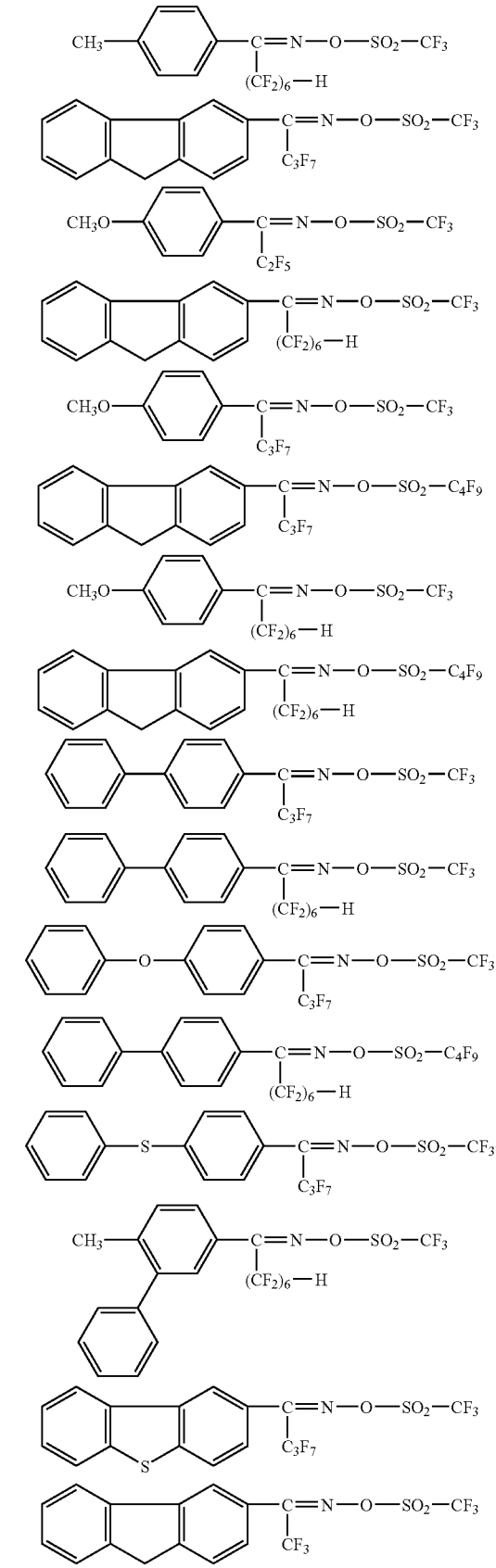

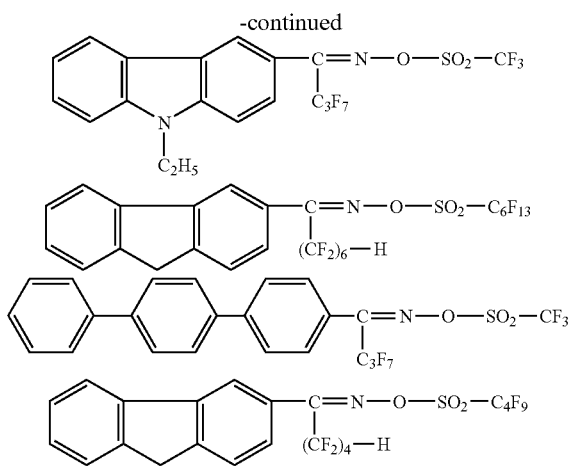

Of the compounds exemplified above, the four compounds shown below are particularly desirable.

[Formula 27]

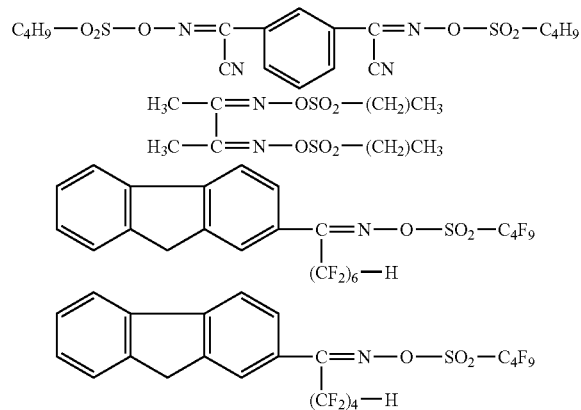

Of the various diazomethane-based acid generators, specific examples of bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Furthermore, the diazomethane-based acid generators disclosed in Japanese Unexamined Patent Application, First Publication No. Hei 11-035551, Japanese Unexamined Patent Application, First Publication No. Hei 11-035552, and Japanese Unexamined Patent Application, First Publication No. Hei 11-035573 can also be used favorably.

Furthermore, specific examples of poly(bis-sulfonyl)diazomethanes include the structures disclosed in Japanese Unexamined Patent Application, First Publication No. Hei 11-322707, such as 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane.

As the component (B), any one of the above acid generators may be used alone, or a combination of two or more different acid generators may be used.

The quantity of the component (B) within the positive resist composition of the present invention is preferably within a range from 0.5 to 30 parts by weight, and even more preferably from 1 to 15 parts by weight, per 100 parts by weight of the component (A). Ensuring a quantity within this range enables satisfactory pattern formation to be conducted. Furthermore, a uniform solution is obtained, and the storage stability is also favorable, both of which are desirable.

[Optional Components]

In the positive resist composition of the present invention, in order to improve the resist pattern shape and the post exposure stability of the latent image formed by the pattern-wise exposure of the resist layer, a nitrogen-containing organic compound (D) (hereafter referred to as the component (D)) may also be added as an optional component.

A multitude of these components (D) have already been proposed, and any of these known compounds can be used. Examples include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylarnine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Of these, secondary aliphatic amines and tertiary aliphatic amines are preferred, trialkylamines of 5 to 10 carbon atoms are even more preferred, and tri-n-octylamine is the most desirable.

These compounds may be used either alone, or in combinations of two or more different compounds.

The component (D) is typically used in a quantity within a range from 0.01 to 5.0 parts by weight per 100 parts by weight of the component (A).

Furthermore, in order to prevent any deterioration in sensitivity caused by the addition of the above component (D), and improve the resist pattern shape and the post exposure stability of the latent image formed by the pattern-wise exposure of the resist layer, an organic carboxylic acid, or a phosphorus oxo acid or derivative thereof (E) (hereafter referred to as the component (E)) may also be added to the positive resist composition of the present invention. The component (D) and the component (E) can be used in combination, or either one can also be used alone.

Examples of suitable organic carboxylic acids include malonic acid, citric acid, malic acid, succinic acid, benzoic acid, and salicylic acid.

Examples of suitable phosphorus oxo acids or derivatives thereof include phosphoric acid or derivatives thereof such as esters, including phosphoric acid, di-n-butyl phosphate and diphenyl phosphate; phosphonic acid or derivatives thereof such as esters, including phosphonic acid, dimethyl phosphonate, di-n-butyl phosphonate, phenylphosphonic acid, diphenyl phosphonate, and dibenzyl phosphonate; and phosphinic acid or derivatives thereof such as esters, including phosphinic acid and phenylphosphinic acid, and of these, phosphonic acid is particularly preferred.

The component (E) is typically used in a quantity within a range from 0.01 to 5.0 parts by weight per 100 parts by weight of the component (A).

Other miscible additives may also be added to the positive resist composition of the present invention according to need, and examples include additive resins for improving the properties of the resist film, surfactants for improving the coating properties, dissolution inhibitors, plasticizers, stabilizers, colorants, halation prevention agents, and dyes.

The positive resist composition can be produced by dissolving the materials in an organic solvent (hereafter also referred to as the component (S)).

The component (S) may be any solvent capable of dissolving the various components to generate a uniform solution, and one or more solvents selected from known materials used as the solvents for conventional chemically amplified resists can be used.

Examples of the solvent include lactones such as γ-butyrolactone;

ketones such as acetone, methyl ethyl ketone, cyclohexanone, methyl n-amyl ketone, methyl isoamyl ketone and 2-heptanone;

polyhydric alcohols such as ethylene glycol, diethylene glycol, propylene glycol and dipropylene glycol, and derivatives thereof;

polyhydric alcohol derivatives including compounds with an ester linkage such as ethylene glycol monoacetate, diethylene glycol monoacetate, propylene glycol monoacetate and dipropylene glycol monoacetate, and compounds with an ether linkage including monoalkyl ethers such as the monomethyl ether, monoethyl ether, monopropyl ether or monobutyl ether, or the monophenyl ether of any of the above polyhydric alcohols or the above compounds with an ester linkage;

cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethyl benzyl ether, cresyl methyl ether, diphenyl ether, dibenzyl ether, phenetole, butyl phenyl ether, ethylbenzene, diethylbenzene, amylbenzene, isopropylbenzene, toluene, xylene, cymene, and mesitylene.

These organic solvents may be used either alone, or as a mixed solvent containing two or more different solvents.

Of these solvents, propylene glycol monomethyl ether acetate (PGMEA), propylene glycol monomethyl ether (PGME), and EL are preferred.

Furthermore, as the solvent (S), mixed solvents produced by mixing PGMEA with a polar solvent are also preferred. Although the blend ratio (the weight ratio) in such mixed solvents can be set in accordance with factors such as the co-solubility of the PGMEA and the polar solvent, the ratio is preferably within a range from 1:9 to 9:1, and is even more preferably from 2:8 to 8:2.

More specifically, in those cases where EL is added as the polar solvent, the weight ratio PGMEA:EL is preferably within a range from 1:9 to 9:1, and is even more preferably from 2:8 to 8:2. Furthermore, in those cases where PGME is used as the polar solvent, the weight ratio PGMEA:PGME is preferably within a range from 1:9 to 9:1, even more preferably from 2:8 to 8:2, and is most preferably from 3:7 to 7:3.

Furthermore, as the component (S), mixed solvents containing at least one of PGMEA and EL, together with γ-butyrolactone, are also preferred. In such cases, the weight ratio of the former and latter components in the mixed solvent is preferably within a range from 70:30 to 95:5.

There are no particular restrictions on the quantity used of the component (S), which can be set in accordance with the coating film thickness required, at a concentration that enables favorable application of the solution to a substrate or the like. Typically, the quantity of the component (S) is set so that the solid fraction concentration of the resist composition is within a range from 2 to 20% by weight, and preferably from 5 to 15% by weight.

Method for Forming a Resist Pattern of the Third Embodiment

A positive resist composition according to the aforementioned second embodiment can be used within a method for forming a resist pattern (a method for forming a resist pattern according to a third embodiment) that includes the steps of: forming a resist film on a substrate using a positive resist composition according to the second embodiment described above, exposing the resist film, and developing the resist film to form a resist pattern.

The method for forming a resist pattern can be conducted, for example, in the manner described below.

In other words, the positive resist composition of the second embodiment described above is first applied to a substrate such as a silicon wafer using a spinner or the like, and an optional prebake (PAB) is then conducted, thereby forming a resist film. Following selective exposure of the thus formed resist film, either by exposure through a mask pattern using an exposure apparatus such as an ArF exposure apparatus, an electron beam lithography apparatus or an EUV exposure apparatus, or by patterning via direct irradiation with an electron beam without using a mask pattern, PEB (post exposure baking) is conducted. Subsequently, developing is conducted using an alkali developing solution, a rinse treatment is performed to wash away the residual developing solution on the substrate and the portions of the resist composition that have been dissolved by the developing solution, and the resist is then dried, yielding a resist pattern.

These steps can be conducted using conventional techniques. The conditions during the operation are preferably set in accordance with factors such as the formulation and properties of the positive resist composition.

There are no particular restrictions on the exposure source, and an ArF excimer laser, KrF excimer laser, $F_2$ excimer laser, or other radiation such as EUV (extreme ultra violet), VUV (vacuum ultra violet), electron beam, X-ray or soft X-ray radiation can be used. The positive resist composition described above is particularly effective for use with an ArF excimer laser, an electron beam or EUV radiation, and an ArF excimer laser or electron beam is particularly desirable.

In some cases, the method may include a post bake step following the above alkali developing step, and an organic or inorganic anti-reflective film may also be provided between the substrate and the resist film.

<Dissolution Inhibitor>

The compound (A1) described above can be used favorably as a dissolution inhibitor for a positive resist composition. By using a dissolution inhibitor formed from the compound (A1), the alkali solubility of the resist film (prior to exposure) obtained using the positive resist composition containing the dissolution inhibitor is inhibited. As a result, when the resist film is selectively exposed, the difference in alkali solubility between the exposed portions and the unexposed portions (the solubility contrast) increases, and a resist pattern with favorable resolution and shape can be formed.

This dissolution inhibitor can be used by addition to a two-component chemically amplified resist composition including a resin component that contains acid-dissociable, dissolution-inhibiting groups, and an acid generator component. Furthermore, the dissolution inhibitor may also be used in a so-called three-component chemically amplified resist composition, which includes a resin component that contains no acid-dissociable, dissolution-inhibiting groups, an acid generator component, and the dissolution inhibitor.

Compound of the Fourth Embodiment

A compound of the fourth embodiment of the present invention (hereafter referred to as the compound (I)) is represented by the general formula (I) shown above. This compound (I) is the same as the compound of the general formula (I) described above in relation to the first embodiment.

In the general formula (I), $R^{11}$ to $R^{17}$, g, j, k, q, a, b, l, m, c, n, o and A are as defined above for $R^{11}$ to $R^{17}$, g, j, k, q, a, b, l, m, c, n, o and A respectively within the above general formula (A-1).

There are no particular restrictions on the bonding positions within the general formula (I) of the carboxyalkyloxy groups [—O—$(CH_2)_a$—CO—OH] bearing the subscripts b and c, but those compounds in which the carboxyalkyloxy groups are bonded at least to the para position relative to the group A that is bonded to the benzene rings to which the carboxyalkyloxy groups are bonded are preferred. These compounds offer certain advantages, including the fact that a low molecular weight compound produced using the compound is ideal for use within a resist composition, and the fact that the compounds are readily synthesized.

There are no particular restrictions on the bonding positions of the hydroxyl groups bearing the subscript g, although in terms of using the compound to produce a low molecular weight compound that is ideal for use within a resist composition, and ensuring ready synthesis, compounds in which hydroxyl groups are bonded to at least the para position (position 4) of the phenyl groups are preferred.

There are no particular restrictions on the bonding positions of the groups $R^{11}$, $R^{12}$ and $R^{17}$, but in terms of factors such as the ease of synthesis, $R^{11}$ is preferably bonded to at least one of the carbon atoms adjacent to a carbon atom bearing a hydroxyl group.

As the compound (I) of the fourth embodiment of the present invention, compounds represented by a general formula (II) shown below can be used to produce a compound that is ideal for use within a resist composition, and are consequently preferred.

[Formula 28]

(II)

In the formula (II), $R^{11}$ to $R^{12}$, a and A are as defined for $R^{11}$ to $R^{12}$, a and A within the formula (I). b' represents an integer from 1 to 4, is preferably either 1 or 2, and is most preferably 1. c' represents an integer from 1 to 4, is preferably either 1 or 2, and is most preferably 1.

Of these compounds, compounds in which both b' and c' are 1 are preferred, and compounds represented by a general formula (II-1) shown below are particularly desirable.

[Formula 29]

(II-1)

[wherein, $R^{11}$ to $R^{12}$, a and A are as defined for $R^{11}$ to $R^{12}$, a and A within the above general formula (I).]

There are no particular restrictions on the bonding position of $R^{12}$, although in terms of ease of synthesis, bonding to the ortho position or meta position relative to the hydroxyl group is preferred.

In other words, as the compound represented by the formula (II), compounds represented by general formulas (II-2) and (II-3) shown below are preferred.

[Formula 30]

(II-2)

-continued

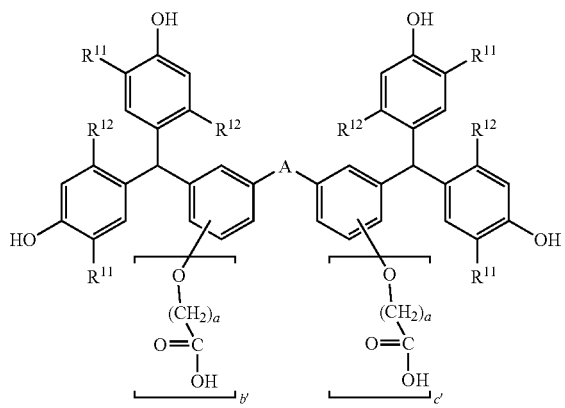

(II-3)

[wherein, $R^{11}$ to $R^{12}$, a and A are as defined for $R^{11}$ to $R^{12}$, a and A within the above general formula (I), and b' and c' are as defined for b' and c' within the above general formula (II).]

The compound (I) is a material that is capable of forming an amorphous (non-crystalline) film using a spin coating method. Here, an amorphous film refers to an optically transparent film that does not crystallize. Spin coating is one of the most commonly used methods for forming thin films.

A judgment as to whether or not the compound is capable of forming an amorphous film using spin coating is determined on the basis of whether or not a film formed by spin coating the compound onto an 8-inch silicon wafer is transparent across the entire film surface. More specifically, judgment can be conducted, for example, in the manner described below. First, the compound is added to a solvent typically used as a resist solvent, such as a mixed solvent of ethyl lactate and propylene glycol monomethyl ether acetate in a ratio (weight ratio) of 40/60 (hereafter this solvent is abbreviated as EM), in sufficient quantity to generate a solution with a concentration of 14% by weight, and dissolution of the compound is achieved by ultrasound treatment (dissolution treatment) using an ultrasonic cleaning apparatus. The resulting solution is spin coated onto a wafer at 1,500 rpm and subjected to optional drying and baking (PAB, Post Applied Bake) at 110° C. for 90 seconds, and a visual judgment is then made as to whether the formed film is transparent, thereby confirming whether or not an amorphous film has been formed. A non-transparent, cloudy film is not an amorphous film.

In the present invention, the compound (I) preferably generates an amorphous film via the above method that exhibits favorable stability, and for example, compounds for which the amorphous state of the film is retained even after standing for 2 weeks at room temperature following the above PAB treatment are particularly desirable.

The compound (I) can be produced by the conventional methods described above, although in this type of conventional method, controlling the hydroxyl group positions where the carboxyalkyloxy groups are introduced and the number of carboxyalkyloxy groups is difficult, and the yield tends to be low for the compound (I) in which carboxyalkyloxy groups are bonded to both of the two benzene rings that are linked via the group A.

As a result, the compound (I) is preferably produced using a production method of the present invention described below.

Method for Producing Compound (I) according to the Fifth Embodiment

A method of producing the compound (I) according to a fifth embodiment includes:

a step of reacting a compound (I-1) represented by the above general formula (I-1) and a compound (I-2) represented by the above general formula (I-2) to obtain a compound (I-3) represented by the above general formula (I-3) (hereafter referred to as the compound (I-3) formation step), and a step of obtaining the compound (I) (hereafter referred to as the compound (I) formation step), via a step of reacting the compound (I-3) and a compound (I-4) represented by the above general formula (I-4) under acidic conditions.

A more detailed description of each of the above steps is provided below.

<Compound (I-3) Formation Step>

In the general formulas (I-1) to (I-3), $R^{13}$ to $R^{16}$, a, b, l, m, c, n, o and A are as defined above for $R^{13}$ to $R^{16}$, a, b, l, m, c, n, o and A respectively within the above general formula (I).

In the general formula (I-2), examples of the halogen atom represented by X include a bromine atom, chlorine atom, and fluorine atom. A bromine atom is preferred as it offers superior reactivity.

There are no particular restrictions on the protective group represented by R, provided it is an acid-dissociable group that does not react during the reaction between the compound (I-1) and the compound (I-2), but then dissociates under the acidic conditions used during reaction of the compound (I-3) in the subsequent compound (I) formation step, and this group may selected from the many groups typically proposed as protective groups.

Examples of such protective groups include any of the groups proposed as acid-dissociable, dissolution-inhibiting groups within the base resins used for conventional chemically amplified positive resist compositions for use with a KrF excimer laser or ArF excimer laser, and specific examples include tertiary alkyl groups, tertiary alkyloxycarbonyl groups, alkoxycarbonylalkyl groups, alkoxyalkyl groups, and cyclic ether groups.

As the tertiary alkyl group, groups of 4 to 12 carbon atoms are preferred, and groups of 4 to 10 carbon atoms are even more desirable. Specific examples include chain-like tertiary alkyl groups such as a tert-butyl group or tert-amyl group, and tertiary alkyl groups that contain an aliphatic cyclic group, such as a 2-methyl-2-adamantyl group or 2-ethyl-2-adamantyl group.

Examples of the tertiary alkyl group within the tertiary alkyloxycarbonyl groups include the same groups as those described above.

Specific examples of the tertiary alkyloxycarbonyl group include a tert-butyloxycarbonyl group and a tert-amyloxycarbonyl group.

Examples of the alkoxycarbonylalkyl group include the same groups as those represented by the general formula (p1) within the first embodiment.

Examples of the alkoxyalkyl group include the same groups as those represented by the general formula (p2) within the first embodiment.

In the formula (p2), examples of the $R^2$ group include straight-chain, branched or cyclic alkyl groups, which may include a hetero atom within the structure, and specific examples of the $R^2$ group include the same groups as those exemplified for $R^1$ within the above general formula (p1).

The group $R^3$ in the general formula (p2) is either a hydrogen atom or a lower alkyl group, in the same manner as the group $R^3$ within the above general formula (p2) of the first embodiment.

In the groups represented by the formula (p2), $R^2$ is preferably a straight-chain alkyl group.

Specific examples of the cyclic ether group include a tetrahydropyranyl group and a tetrahydropyranyl group.

The compound (I-1) and the compound (I-2) can be reacted using conventional methods, in a similar manner to that described for the compound (I-3) formation step within the first embodiment. For example, reaction can be conducted by dissolving the compound (I-1) in an organic solvent such as acetone, adding a base such as potassium carbonate to the solution, and then adding the compound (I-2) to the stirred solution of the compound (I-1), in a quantity that provides approximately 2 molar equivalents of the compound (I-2) relative to the compound (I-1).

In the same manner as that described for the compound (I-3) formation step within the first embodiment, the organic solvent used during this reaction may be any solvent capable of dissolving the compound (I-1), the compound (I-2) and the produced compound (I-3), and may be selected appropriately from typical organic solvents.

The reaction temperature is preferably within a range from 10 to 60° C., even more preferably from 20 to 60° C., and can usually be set to room temperature (20 to 25° C.).

The reaction time is preferably within a range from 1 to 24 hours, and is even more preferably from 4 to 15 hours.

Following completion of the reaction, the reaction solution may be used, as is, in the following step, or water/ethyl acetate or the like may be added, and the organic phase (the phase containing the ethyl acetate or the like) then concentrated under reduced pressure to obtain the compound (I-3).

<Compound (I) Formation Step>

In the general formula (I-4), $R^{11}$, $R^{12}$, $R^{17}$, g, j, k and q are as defined above for g, j, k and q respectively within the above general formula (I).

The compound (I) formation step of this embodiment is the same as the compound (I) formation step described above for the first embodiment. This step yields the compound (I).

This unpurified compound (I) may be subjected to a purification treatment such as re-precipitation.

The above compound (I) of the present invention can be used favorably for the production of a low molecular weight compound that can be used within a resist composition.

For example, the compound (I) can be used favorably for the production of a compound represented by the above general formula (A-1) (hereafter referred to as the low molecular weight compound (A1)). This low molecular weight compound (A1) is the same as the compound (A1) of the first embodiment.

The low molecular weight compound (A1) is a compound in which a portion of, or all of, the carboxyl groups of the compound (I) have been protected with acid-dissociable, dissolution-inhibiting groups.

The acid-dissociable, dissolution-inhibiting group is a group that exhibits an alkali dissolution-inhibiting effect that renders the low molecular weight compound (A1) insoluble in alkali prior to dissociation, but then upon dissociation, causes the entire low molecular weight compound (A1) to change to an alkali-soluble state. Accordingly, when the low molecular weight (A1) is blended into a positive resist composition together with an acid generator component, the action of the acid generated from the acid generator component by exposure causes the acid-dissociable, dissolution-inhibiting groups to dissociate, thereby increasing the alkali solubility. As a result, a positive resist pattern can be formed by conducting alkali developing.

Furthermore, in a similar manner to the compound (I), the low molecular weight compound (A1) is a material that is capable of forming an amorphous (non-crystalline) film using a spin coating method.

Accordingly, the low molecular weight compound (A1) is useful as a base material component for a positive resist composition.

There are no particular restrictions on the acid-dissociable, dissolution-inhibiting groups represented by R' in the above general formula (A-1), which may be selected appropriately from those groups proposed for use within the hydroxystyrene-based resins and (meth)acrylate-based resins and the like used in chemically amplified positive resist compositions designed for use with KrF or ArF excimer lasers. Specific examples include the protective groups R exemplified above in relation to the general formulas (I-2) and (I-3).

The low molecular weight compound (A1) can be produced, for example, by using known methods to substitute either a portion of, or all of, the hydrogen atoms at the terminals of the carboxyl groups of one or more compounds (I) with acid-dissociable, dissolution-inhibiting groups.

The above low molecular weight compound (A1) can be used favorably as a base material component (A) within a positive resist composition that includes the base material component (A), which exhibits increased alkali solubility under the action of acid, and an acid generator component (B) that generates acid upon irradiation.

For example, the actions and effects of this low molecular weight compound (A1) are the same as the actions and effects of the compound (A1) of the first embodiment, meaning that by using a positive resist composition that includes the low molecular weight compound (A1), a high resolution resist pattern can be formed, and the roughness can also be reduced.

Moreover, as described above, because the low molecular weight compound (A1) (the compound (A1)) exhibits uniform properties, and is thought to be capable of forming a resist film with uniform properties (such as the alkali solubility, the hydrophilicity and the hydrophobicity), using the low molecular weight compound (A1) can reduce the level of defects.

Furthermore, because the low molecular weight compound (A1) exhibits uniform properties, and is thought to display uniform solubility in organic solvents and the like, the storage stability of a positive resist composition containing the low molecular weight compound (A1) also improves.

A positive resist composition of the sixth embodiment that uses this type of low molecular weight compound (A1) (the compound (A1)) is similar to the positive resist composition of the second embodiment.

Method for Forming a Resist Pattern of the Seventh Embodiment

A positive resist composition according to the aforementioned sixth embodiment can be used within a method for forming a resist pattern (according to a seventh embodiment) that includes the steps of: forming a resist film on a substrate using a positive resist composition according to the sixth embodiment, exposing the resist film, and developing the resist film to form a resist pattern.

The method for forming a resist pattern according to the seventh embodiment can be conducted in the same manner as that described for the method for forming a resist pattern of the third embodiment.

<Dissolution Inhibitor>

The low molecular weight compound (A1) described above can also be used favorably as a dissolution inhibitor for a positive resist composition.

EXAMPLES

As follows is a description of examples of the present invention, although the scope of the present invention is in no way limited by these examples.

Synthesis Example 1

Synthesis of a Compound (1)

30 g of methylene bis-salicylaldehyde (1') (manufactured by Honshu Chemical Industry Co., Ltd.) was dissolved by adding 500 g of acetone. To the resulting solution was added 48.6 g of potassium carbonate ($K_2CO_3$), and the mixture was stirred for 10 minutes at room temperature. Subsequently, 45.72 g of tert-butyl bromoacetate (2') was added, and the resulting mixture was reacted at room temperature (r.t) for 12 hours.

Following completion of the reaction, the reaction mixture was extracted using water/ethyl acetate (weight ratio 1:1), and the ethyl acetate phase was concentrated under reduced pressure, yielding 53.5 g of the target compound (3').

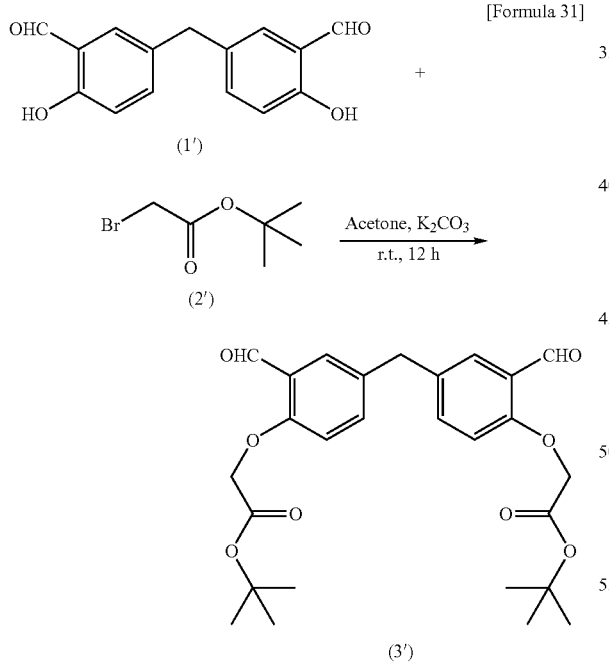

Subsequently, 12 g of the compound (3') was added to a mixed solution containing 15.14 g of 2,5-dimethylphenol (4'), 50 g of methanol ($CH_3OH$) and 10 g of a 35% by weight aqueous solution of hydrochloric acid (HCl aq.), and the resulting mixture was reacted for 3 days at 60° C.

Following completion of the reaction, the reaction mixture was returned to room temperature, an aqueous solution of sodium hydroxide was added, and the resulting mixture was stirred for 10 hours. Subsequently, the reaction solution was transferred to a separating funnel, and following washing with water/diethyl ether to remove any raw materials, the water phase was extracted and then neutralized with an aqueous solution of hydrochloric acid (with the neutrality determined using pH test paper), thereby yielding a precipitate. This precipitate was collected by filtration, yielding crude crystals. These crude crystals were dissolved in tetrahydrofuran (THF), and then re-precipitated using heptane. Subsequently, the precipitate was collected by filtration, yielding crude crystals. These crude crystals were dissolved in THF, and then concentrated and dried, yielding 15.3 g of the target compound (1).

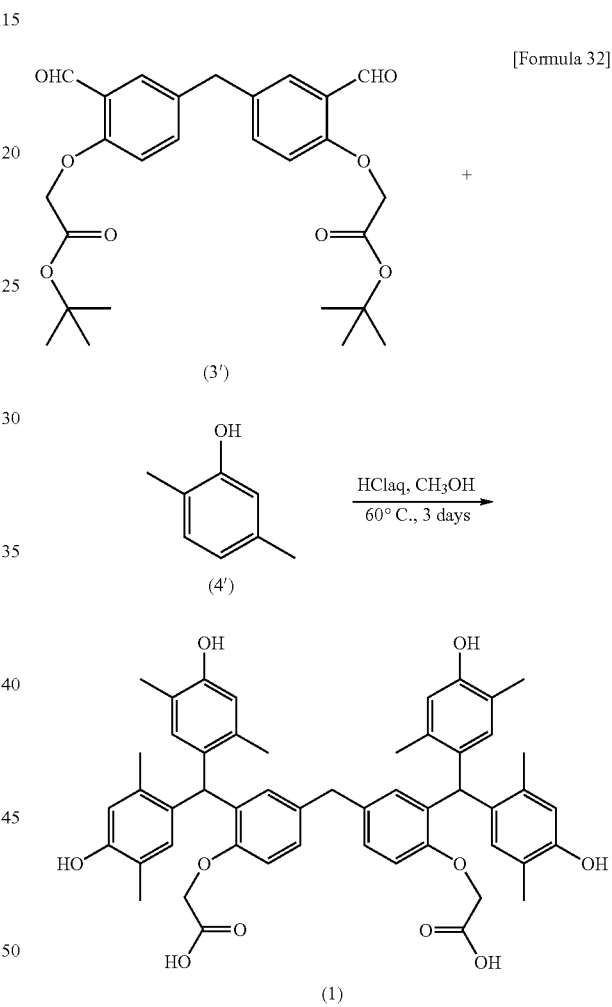

The compound (1) was analyzed using $^1$H-NMR (proton nuclear magnetic resonance spectroscopy) and IR (infrared spectroscopy). The results are shown below.

$^1$H-NMR data (deuterated dimethylsulfoxide (DMSO-d6), 400 MHz, internal standard: tetramethylsilane): δ (ppm)= 12.68 brs 2H H$^a$, 8.94 brs 4H H$^b$, 6.82 to 6.27 m 14H H$^c$, 5.85 s 2H H$^d$, 4.47 s 4H H$^e$, 3.32 s 2H H$^f$, 2.09 to 1.76 brs 24H H$^g$.

IR data: 3382 cm$^{-1}$, 2925 cm$^{-1}$, 1728 cm$^{-1}$, 1495 cm$^{-1}$, 1463 cm$^{-1}$, 1411 cm$^{-1}$, 1285 cm$^{-1}$, 1227 cm$^{-1}$, 1195 cm$^{-1}$, 1119 cm$^{-1}$, 1075 cm$^{-1}$.

These results confirmed that the compound (1) had the structure shown below.

[Formula 33]

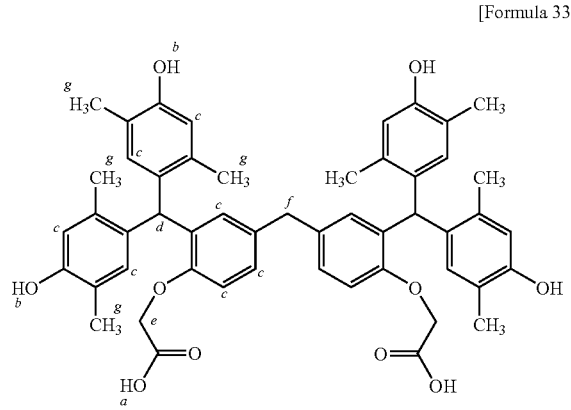

Synthesis Example 2

Synthesis of a Compound (3)

12 g of the compound (3') obtained in the same manner as the synthesis example 1 was added to a mixed solution containing 21.23 g of 2-cyclohexyl-5-methylphenol (8'), 50 g of methanol and 10 g of a 35% by weight aqueous solution of hydrochloric acid, and the resulting mixture was reacted for 3 days at 60° C.

Following completion of the reaction, the reaction mixture was returned to room temperature, an aqueous solution of sodium hydroxide was added, and the resulting mixture was stirred for 10 hours. Subsequently, the reaction solution was transferred to a separating funnel, and following washing with water/diethyl ether to remove any raw materials, the water phase was extracted and then neutralized with an aqueous solution of hydrochloric acid (with the neutrality determined using pH test paper), thereby yielding a precipitate. This precipitate was collected by filtration, yielding crude crystals. These crude crystals were dissolved in tetrahydrofuran (THF), and then re-precipitated using heptane. Subsequently, the precipitate was collected by filtration, yielding crude crystals. These crude crystals were dissolved in THF, and then concentrated and dried, yielding 16.0 g of the target compound (3).

[Formula 34]

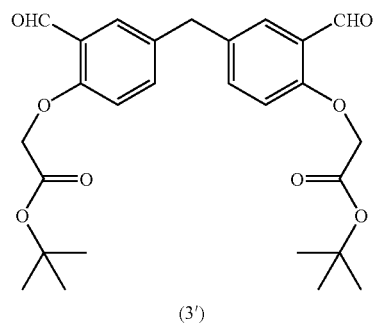

+

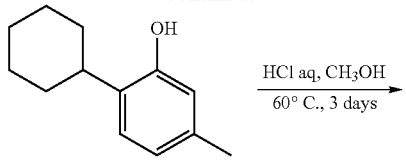

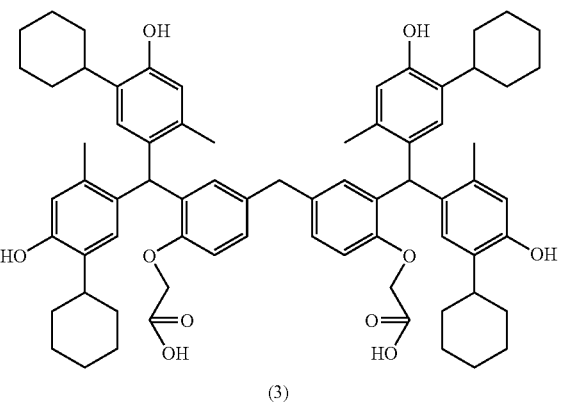

The compound (3) was analyzed using $^1$H-NMR and IR. The results are shown below.

$^1$H-NMR data (deuterated dimethylsulfoxide (DMSO-d6), 400 MHz, internal standard: tetramethylsilane): δ (ppm)= 8.94 brs 4H H$^a$, 6.79 to 6.40 m 14H H$^b$, 5.92 s 2H H$^c$, 4.35 s 4H H$^d$, 3.48 s 2H H$^e$, 2.81 to 2.59 m 4H H$^f$, 2.01 s 12H Hg, 1.70 to 0.89 m 40H, H$^h$.

IR data: 3367 cm$^{-1}$, 2925 cm$^{-1}$, 2851 cm$^{-1}$, 1736 cm$^{-1}$, 1494 cm$^{-1}$, 1449 cm$^{-1}$, 1415 cm$^{-1}$, 1282 cm$^{-1}$, 1223 cm$^{-1}$, 1157 cm$^{-1}$, 1118 cm$^{-1}$, 1053 cm$^{-1}$.

These results confirmed that the compound (3) had the structure shown below.

[Formula 35]

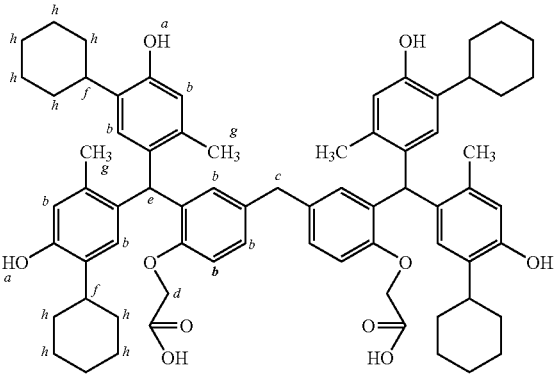

Synthesis Example 3

Synthesis of a Compound (2)

5 g of the compound (1) was dissolved in 30 g of tetrahydrofuran (THF), 1.52 g of triethylamine (Et₃N) was added, the resulting mixture was stirred for 10 minutes, 2.43 g of 2-chloromethoxyadamantane was added, and the resulting mixture was stirred for 10 hours at room temperature. Following completion of the reaction, the reaction mixture was filtered, the resulting filtrate was extracted by addition of water/ethyl acetate (weight ratio 1:1), and the separated ethyl acetate phase was concentrated under reduced pressure, yielding 5.1 g of the target compound (2).

[Formula 36]

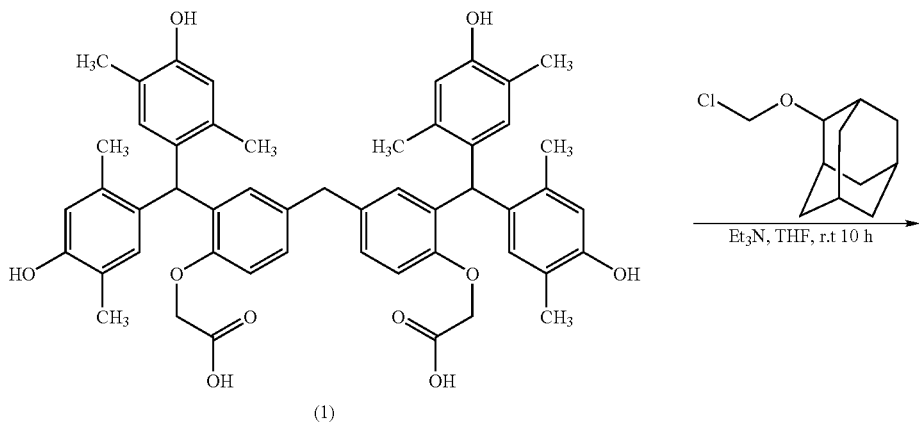

The compound (2) was analyzed using $^1$H-NMR and IR.
$^1$H-NMR data (deuterated dimethylsulfoxide (DMSO-d6), 400 MHz, internal standard: tetramethylsilane): δ (ppm)= 8.80 brs 4H H$^a$, 6.24 to 6.72 m 14H H$^b$, 5.83 s 2H H$^c$, 5.36 s 4H H$^d$, 4.61 s 4H H$^e$, 3.66 s 2H H$^f$, 3.57 s 2H H$^g$, 1.95 s 12H H$^h$, 1.85 s 12H H$^i$, 1.29 to 2.15 m 28H, H$^j$.

IR data: 3391 cm$^{-1}$, 2907 cm$^{-1}$, 2855 cm$^{-1}$, 1737 cm$^{-1}$, 1496 cm$^{-1}$, 1286 cm$^{-1}$.

These results confirmed that the compound (2) had the structure shown below. In the structure shown below, f represents the hydrogen atom within the 2-adamantyl groups that is bonded to the carbon atom bonded directly to the oxygen atom, whereas j represents the hydrogen atoms besides f within the 2-adamantyl groups.

[Formula 37]

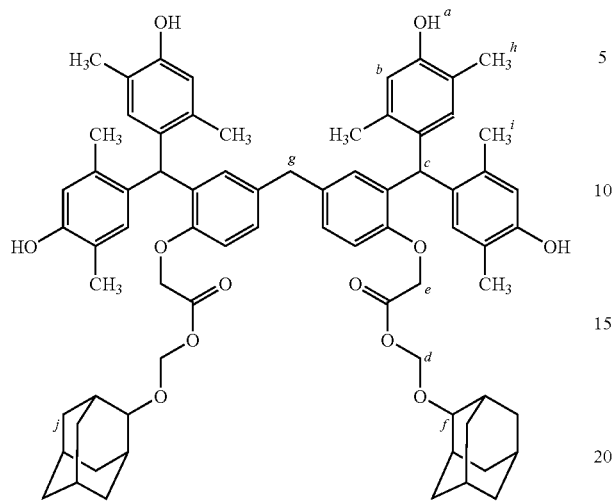

Synthesis Example 4

Synthesis of a Compound (4)

3 g of the compound (3) was dissolved in 30 g of THF, 0.81 g of Et$_3$N was added, the resulting mixture was stirred for 10 minutes, 1.10 g of 2-chloromethoxyadamantane was added, and the resulting mixture was stirred for 10 hours at room temperature. Following completion of the reaction, the reaction mixture was filtered, the resulting filtrate was extracted by addition of water/ethyl acetate (weight ratio 1:1), and the separated ethyl acetate phase was concentrated under reduced pressure, yielding 3.2 g of the target compound (4).

[Formula 38]

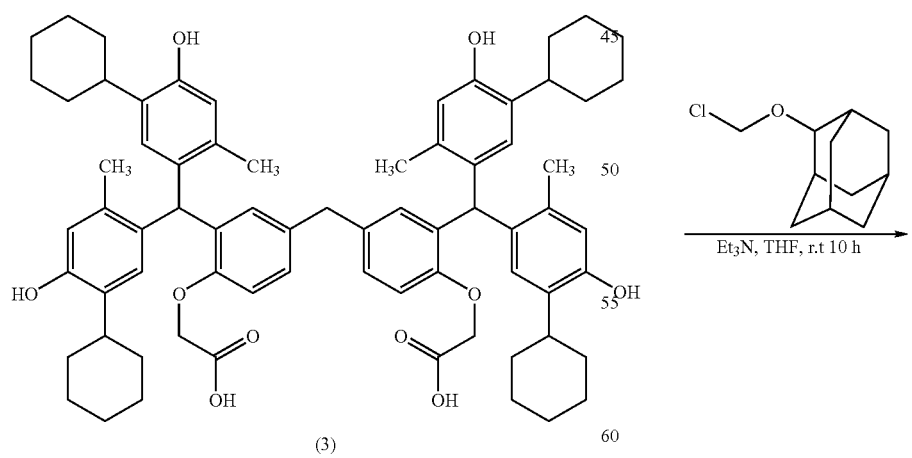

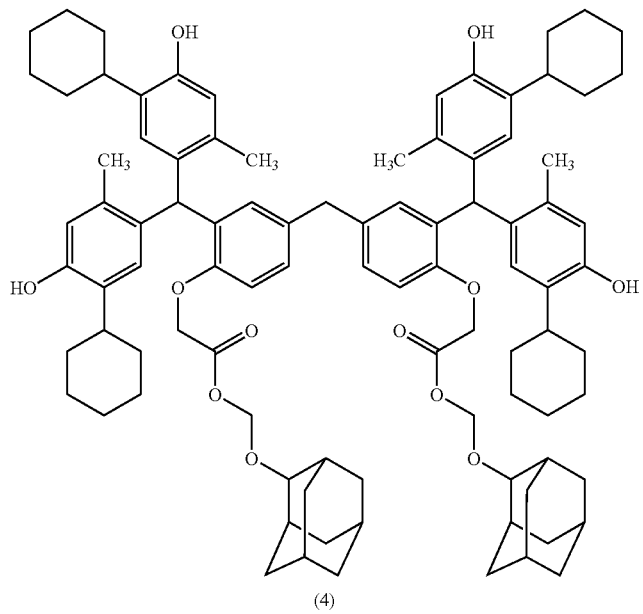

(4)

The compound (4) was analyzed using $^1$H-NMR and IR.

$^1$H-NMR data (deuterated dimethylsulfoxide (DMSO-d6), 400 MHz, internal standard: tetramethylsilane): δ (ppm)= 8.79 brs 4H H$^a$, 6.45 to 6.78 m 14H H$^b$, 5.89 s 2H H$^c$, 5.36 s 4H H$^d$, 4.55 s 4H H$^e$, 3.61 s 2H H$^f$, 3.48 s 2H Hg, 2.62 to 2.80 m 4H H$^h$, 2.02 s 12H H$^i$, 0.98 to 2.16 m 68H, H$^j$.

IR data: 3387 cm$^{-1}$, 2924 cm$^{-1}$, 2852 cm$^{-1}$, 1736 cm$^{-1}$, 1496 cm$^{-1}$, 1450 cm$^{-1}$.

These results confirmed that the compound (4) had the structure shown below. In the structure shown below, f represents the hydrogen atom within the 2-adamantyl groups that is bonded to the carbon atom bonded directly to the oxygen atom, h represents the hydrogen atom within the cyclohexyl groups that is bonded to the carbon atom bonded directly to the phenyl group, and j represents the hydrogen atoms besides f and h within the 2-adamantyl groups and cyclohexyl groups.

[Formula 39]

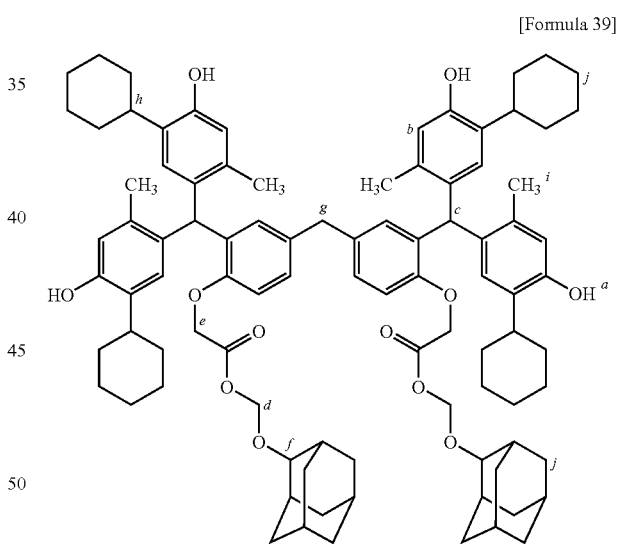

Synthesis Example 5

Synthesis of a Compound (5))

4 g of the compound (1) was dissolved in 20 g of THF, 1.52 g of Et$_3$N was added, the resulting mixture was stirred for 10 minutes, 2.79 g of 2-methyl-2-adamantyl bromoacetate was added, and the resulting mixture was stirred for 10 hours at room temperature. Following completion of the reaction, the reaction mixture was filtered, the resulting filtrate was extracted by addition of water/ethyl acetate (weight ratio 1:1), and the separated ethyl acetate phase was concentrated under reduced pressure, yielding 3.2 g of the target compound (5).

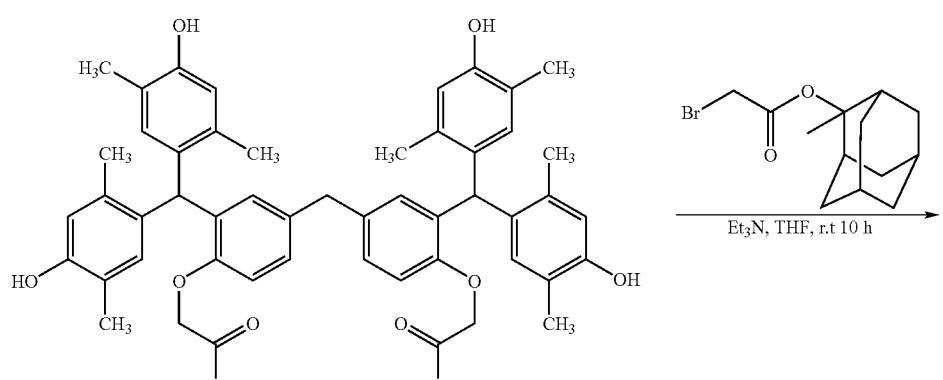

[Formula 40]

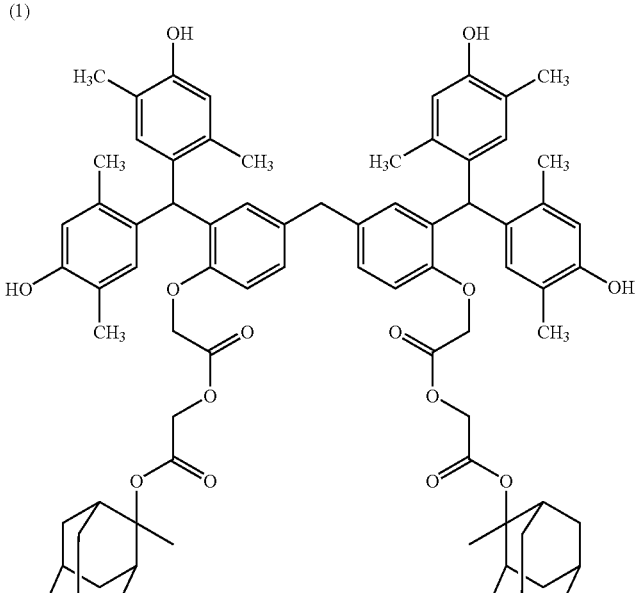

The compound (5) was analyzed using $^1$H-NMR and IR.

$^1$H-NMR data (deuterated dimethylsulfoxide (DMSO-d6), 400 MHz, internal standard: tetramethylsilane): δ (ppm)= 8.80 brs 4H H$^a$, 6.23 to 6.94 m 14H H$^b$, 5.84 s 2H H$^c$, 4.68 s 4H H$^d$, 4.68 s 4H H$^e$, 3.58 s 2H H$^f$, 2.19 s 4H H$^g$, 1.39 to 2.15 m 54H, H$^h$.

IR: 3417 cm$^{-1}$, 2920 cm$^{-1}$, 2863 cm$^{-1}$, 1750 cm$^{-1}$, 1728 cm$^{-1}$, 1495 cm$^{-1}$, 1292 cm$^{-1}$, 1278 cm$^{-1}$.

These results confirmed that the compound (5) had the structure shown below. In the structure shown below, g represents the hydrogen atoms (2 atoms×2) within the 2-methyl-2-adamantyl groups that are bonded to those carbon atoms that are adjacent to the carbon atom bonded directly to the oxygen atom (these carbon atoms constitute part of the ring skeleton), and h represents the hydrogen atoms besides g within the 2-methyl-2-adamantyl groups, and the hydrogen atoms of the methyl groups bonded to the benzene rings.

[Formula 41]

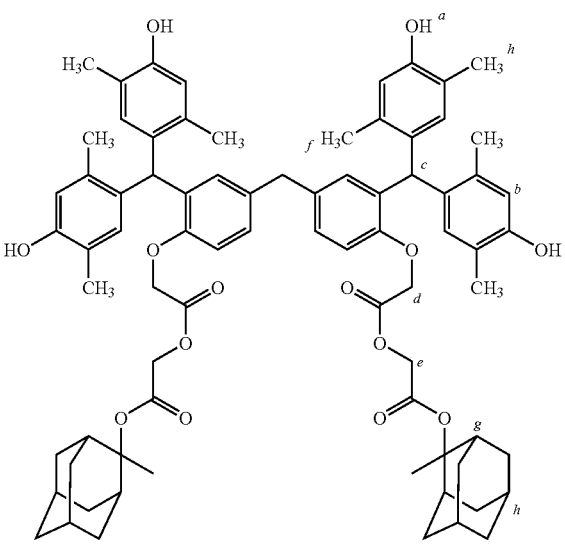

Synthesis Example 6

Synthesis of a Compound (6)

2.7 g of the compound (3) was dissolved in 20 g of THF, 0.61 g of Et$_3$N was added, the resulting mixture was stirred for 10 minutes, 0.80 g of chloromethoxymethylcyclohexane was added, and the resulting mixture was stirred for 10 hours at room temperature. Following completion of the reaction, the reaction mixture was filtered, the resulting filtrate was extracted by addition of water/ethyl acetate (weight ratio 1:1), and the separated ethyl acetate phase was concentrated under reduced pressure, yielding 2.6 g of the target compound (6).

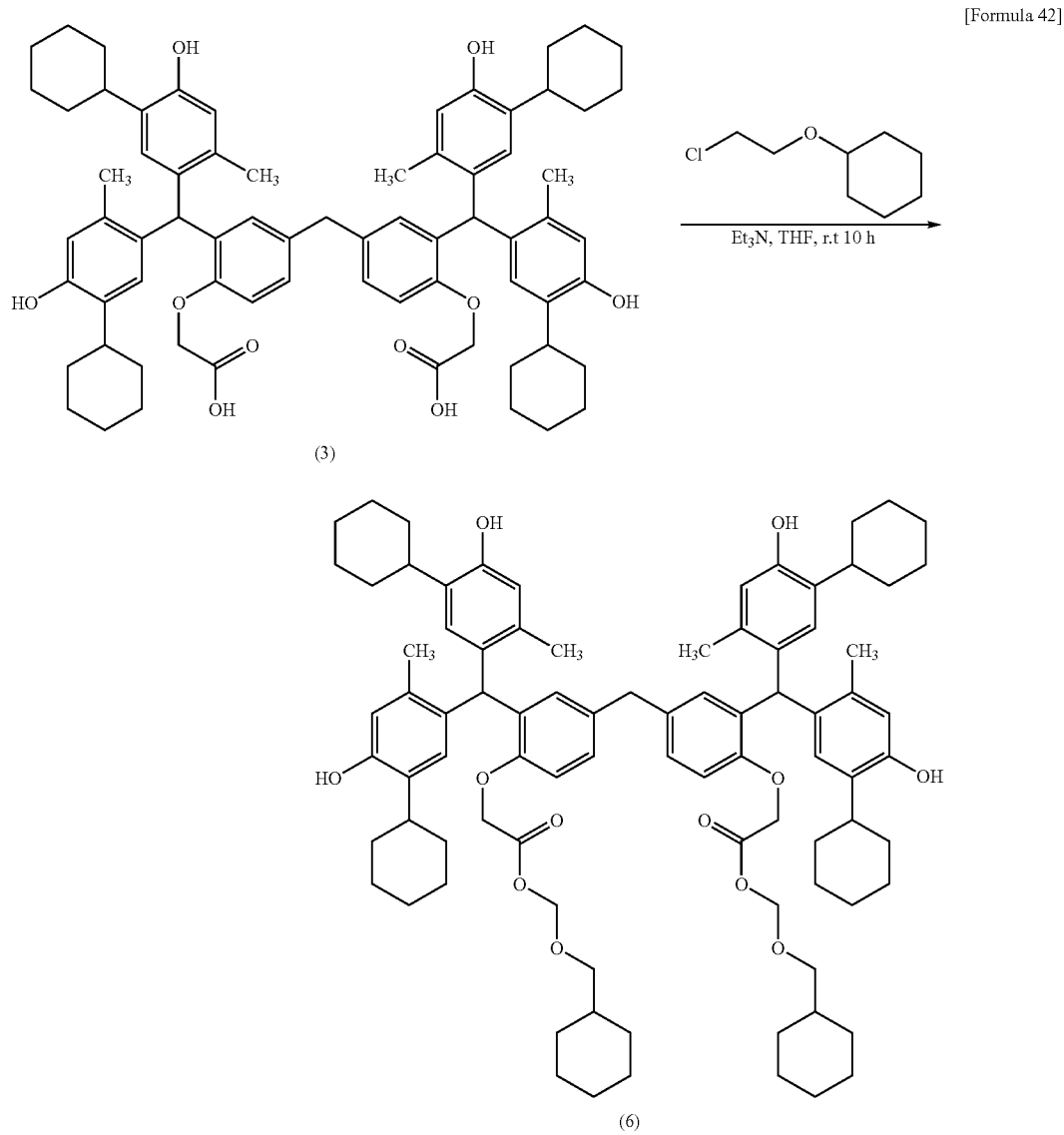

[Formula 42]

The compound (6) was analyzed using $^1$H-NMR and IR.

$^1$H-NMR data (deuterated dimethylsulfoxide (DMSO-d6), 400 MHz, internal standard: tetramethylsilane): δ (ppm)= 8.79 brs 4H H$^a$, 6.38 to 6.86 m 14H H$^b$, 5.92 s 2H H$^c$, 5.26 s 4H H$^d$, 4.60 s 4H H$^e$, 3.51 s 2H H$^f$, 3.28 to 3.29 m 4H H$^g$, 2.62 to 2.81 m 4H H$^i$, 2.01 s 12H H$^j$, 0.75 to 1.82 m 62H H$^k$.

IR: 3405 cm$^{-1}$, 2925 cm$^{-i}$, 2852 cm$^{-1}$, 1755 cm$^{-1}$, 1494 cm$^{-1}$, 1449 cm$^{-1}$, 1280 cm$^{-1}$.

These results confirmed that the compound (6) had the structure shown below. In the structure shown below, i represents the hydrogen atom within the cyclohexyl groups that is bonded to the carbon atom bonded directly to the benzene ring.

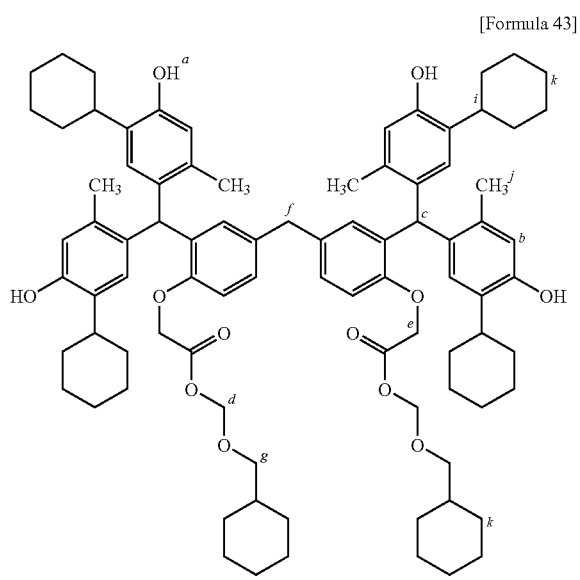

[Formula 43]

Synthesis of Compound (7)

12 g of the compound (3') obtained in the same manner as the synthesis example 1 was added to a mixed solution containing 21.20 g of 2,6-dimethylphenol (9'), 50 g of methanol (CH$_3$OH) and 10 g of a 35% by weight aqueous solution of hydrochloric acid (HCl aq.), and the resulting mixture was reacted for 3 days at 60° C.

Following completion of the reaction, the reaction mixture was returned to room temperature, an aqueous solution of sodium hydroxide was added, and the resulting mixture was stirred for 10 hours. Subsequently, the reaction solution was transferred to a separating funnel, and following washing with water/diethyl ether to remove any raw materials, the water phase was extracted and then neutralized with an aqueous solution of hydrochloric acid (with the neutrality determined using pH test paper), thereby yielding a precipitate. This precipitate was collected by filtration, yielding crude crystals. These crude crystals were dissolved in tetrahydrofuran (THF), and then re-precipitated using heptane. Subsequently, the precipitate was collected by filtration, yielding crude crystals. These crude crystals were dissolved in THF, and then concentrated and dried, yielding 15.0 g of the target compound (7).

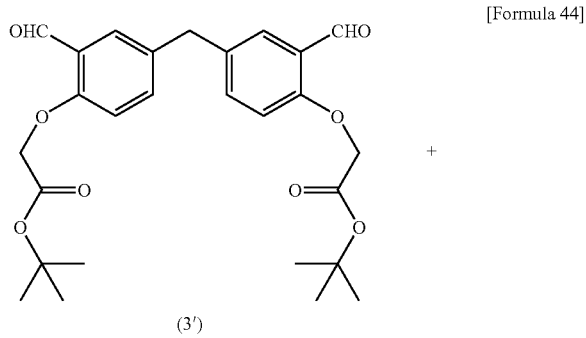

[Formula 44]

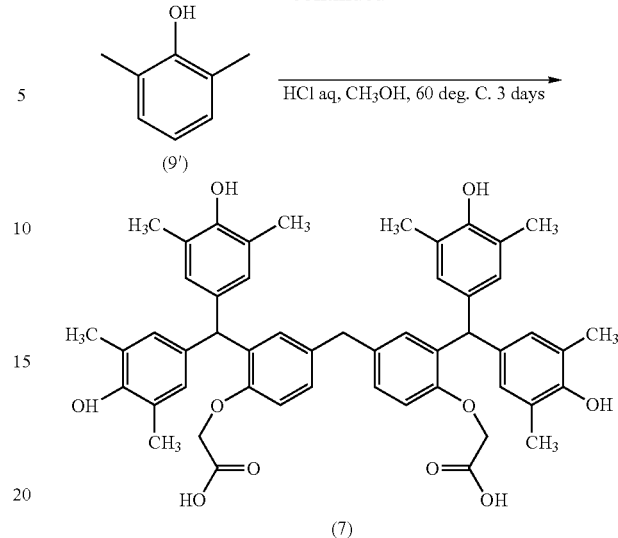

The compound (7) was analyzed using $^1$H-NMR and IR. The results are shown below.

$^1$H-NMR data (deuterated dimethylsulfoxide (DMSO-d6), internal standard: tetramethylsilane, 400 MHz): δ (ppm)= 12.85 brs 2H (H$^a$), 7.91 s 4H (H$^b$), 6.82 to 6.51 m 14H (H$^c$), 5.66 s 2H(H$^d$), 4.51 s 4H (H$^e$), 3.62 s 2H(H$^f$), 2.01 s 24H (H$^g$).

IR data: 3391, 2919, 1736, 1489, 1439, 1290, 1215, 1150, 1116, 1023 cm$^{-1}$.

These results confirmed that the compound (7) had the structure shown below.

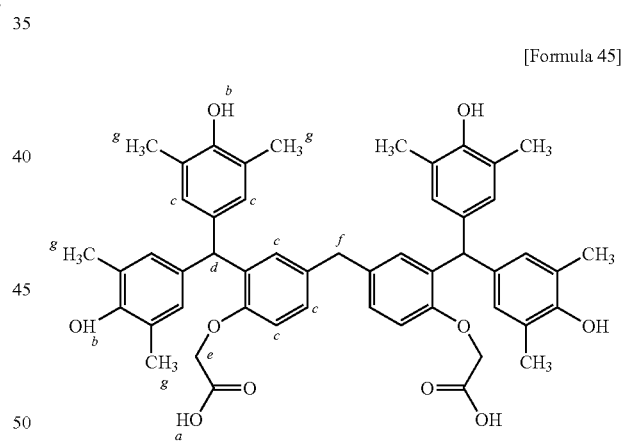

[Formula 45]

Examples 1 to 2

Electron Beam Exposure

The components shown in Table 1 were mixed together and dissolved in the blend quantities shown, yielding positive resist composition solutions.

In Table 1, the units for the blend quantities within the brackets [ ] are parts by weight.

Furthermore, the abbreviations used within Table 1 have the meanings shown below.

TPS-PFBS: triphenylsulfonium nonafluorobutanesulfonate

Amine 1: tri-n-octylamine.

PGMEA: propylene glycol monomethyl ether acetate
EL: ethyl lactate

TABLE 1

|  | Component (A) [blend quantity] | Component (B) [blend quantity] | Component (D) [blend quantity] | Component (S) [blend quantities] | |
|---|---|---|---|---|---|
| Example 1 | Compound (2) [100] | TPS-PFBS [10] | Amine 1 [1] | PGMEA [820] | EL [550] |
| Example 2 | Compound (4) [100] | TPS-PFBS [10] | Amine 1 [1] | PGMEA [820] | EL [550] |

Using the thus obtained positive resist compositions, evaluations were conducted in the manner described below. The results are shown in Table 2. The abbreviation used in Table 2 has the meaning shown below.
EB: Electron Beam
<Sensitivity>

Each of the positive resist composition solutions was applied uniformly, using a spinner, to the surface of an 8-inch silicon substrate that had been treated with hexamethyldisilazane, and was then subjected to a bake treatment (PAB) at 110° C. for 90 seconds, thus forming a resist film (film thickness: 150 nm).

This resist film was then subjected to direct patterning (exposure) with an electron beam lithography apparatus HL-800D (VSB) (manufactured by Hitachi Ltd.) at an accelerating voltage of 70 kV, and was then subjected to a bake treatment (PEB) at 100° C. for 90 seconds, developed for 60 seconds in a 2.38% by weight aqueous solution (at 23° C.) of tetramethylammonium hydroxide (TMAH), and rinsed in pure water for 30 seconds, thus forming a line and space (L/S) pattern.

For this process, the exposure dose Eop ($\mu C/cm^2$) at which a 100 nm L/S pattern was formed in a 1:1 ratio was determined.
<Resolution>

The critical resolution (nm) at the above Eop value was determined using a scanning electron microscope S-9220 (manufactured by Hitachi, Ltd.).

TABLE 2

|  | Radiation source | Eop | Resolution |
|---|---|---|---|
| Example 1 | EB | 42 $\mu C/cm^2$ | 70 nm |
| Example 2 | EB | 59 $\mu C/cm^2$ | 100 nm |

As is evident from the above results, by using the positive resist compositions of the examples 1 and 2, which used the compounds (2) and (4) of the present invention respectively, resist patterns with favorable sensitivity and a high level of resolution were able to be formed.

Example 3

EUV Exposure

With the exception of altering the quantities of the organic solvents used as the component (S) to 1200 parts by weight of PGMEA and 800 parts by weight of EL, positive resist compositions were prepared in the same manner as the example 1.

Subsequently, each of the positive resist composition solutions was applied uniformly, using a spinner, to the surface of an 8-inch silicon substrate that had been treated with hexamethyldisilazane, and was then subjected to a PAB treatment under bake (PAB) conditions at 110° C. for 90 seconds, thus forming a resist film (film thickness: 80 nm).

This resist film was then subjected to exposure with an EUV exposure apparatus HiNA3 (an exposure device owned by the Association of Super-Advanced Electronics Technologies (ASET)), and was then subjected to a PEB treatment under bake (PEB) conditions at 100° C. for 90 seconds, developed for 60 seconds in a 2.38% by weight aqueous solution of TMAH, and rinsed in pure water for 30 seconds, thus forming a L/S pattern.

When the thus obtained resist patterns were evaluated in the same manner as that described above, resolution of a 28 nm line and space pattern (pitch: 56 nm) was confirmed, and the sensitivity for this pattern was 10 $mJ/cm^2$.

Furthermore, for the 28 nm L/S pattern obtained at the above sensitivity, unevenness within the side walls of the pattern was inspected using a SEM (scanning electron microscope, manufactured by Hitachi, Ltd., product name: S-9220). No pattern unevenness was visible, confirming that the level of LER was very favorable.

Furthermore, for a 45 nm L/S pattern, measurement of the 3σ value, which is an indicator of the LER, using a SEM (scanning electron microscope, manufactured by Hitachi, Ltd., product name: S-9380) (measurement length: 600 nm) revealed a value of 2.8 nm.

As is evident from the above results, by using a positive resist composition that uses a compound of the present invention, EUV exposure was able to achieve resolution of a 1:1 28 nm line and space pattern, which represents an ultra fine pattern. Furthermore, the resulting resist pattern showed no visible unevenness in the side walls, confirming a favorable level of LER.

Example 4

Electron Beam Patterning

With the exception of replacing the compound (2) with the compound (5), a positive resist composition was prepared in the same manner as the example 1.

Subsequently, the thus obtained positive resist composition solution was applied uniformly, using a spinner, to the surface of an 8-inch silicon substrate that had been treated with hexamethyldisilazane, and was then subjected to a PAB treatment at 110° C. for 90 seconds, thus forming a resist film (film thickness: 150 nm).

This resist film was then subjected to direct patterning with an electron beam lithography apparatus (HL-800D, manufactured by Hitachi Ltd., accelerating voltage: 70 kV), and was then subjected to a PEB treatment at 100° C. for 90 seconds, developed for 60 seconds in a 2.38% by weight aqueous solution (at 23° C.) of TMAH, and rinsed in pure water for 30 seconds, thus forming a resist pattern.

Evaluation of the obtained resist pattern using the same methods as those described above confirmed resolution of a L/S pattern with a line width of 100 nm and a pitch of 200 nm.

The sensitivity (optimum exposure) for formation of the above L/S pattern was 40 μC/cm². Furthermore, the critical resolution at this sensitivity was 60 nm.

As is evident from the above results, by using a positive resist composition that uses a compound of the present invention, electron beam patterning was able to be used to form a high resolution resist pattern with favorable sensitivity.

Example 5

EUV Exposure

Using the positive resist composition prepared in the example 4, EUV exposure was conducted in the same manner as the example 3, thus forming a resist pattern. When the thus obtained resist pattern was evaluated in the same manner as that described above, resolution of a 28 nm line and space pattern (pitch: 56 nm) was confirmed, and the sensitivity for this pattern was 12.2 mJ/cm².

Furthermore, for the 28 nm L/S pattern obtained at the above sensitivity, unevenness within the side walls of the pattern was inspected using a SEM (scanning electron microscope, manufactured by Hitachi, Ltd., product name: S-9220). No pattern unevenness was visible, confirming that the level of LER was very favorable.

Furthermore, for a 45 nm L/S pattern, measurement of the 3σ value, which is an indicator of the LER, using a SEM (scanning electron microscope, manufactured by Hitachi, Ltd., product name: S-9380) (measurement length: 600 nm) revealed a value of 2.8 nm.

As is evident from the above results, by using a positive resist composition that uses a compound of the present invention, EUV exposure was able to achieve resolution of a 1:1 28 nm line and space pattern, which represents an ultra fine pattern. Furthermore, the resulting resist pattern showed no visible unevenness in the side walls, confirming a favorable level of LER.

INDUSTRIAL APPLICABILITY

The present invention is able to provide a compound that can be used within a resist composition, a positive resist composition containing the compound, and a method for forming a resist pattern that uses the positive resist composition.

Furthermore, the present invention can also provide a compound that can be used favorably for the production of a low molecular weight compound that can be used within a resist composition, and a method for producing the compound.

The invention claimed is:

1. A compound represented by a general formula (A-1) shown below:

[Formula 1]

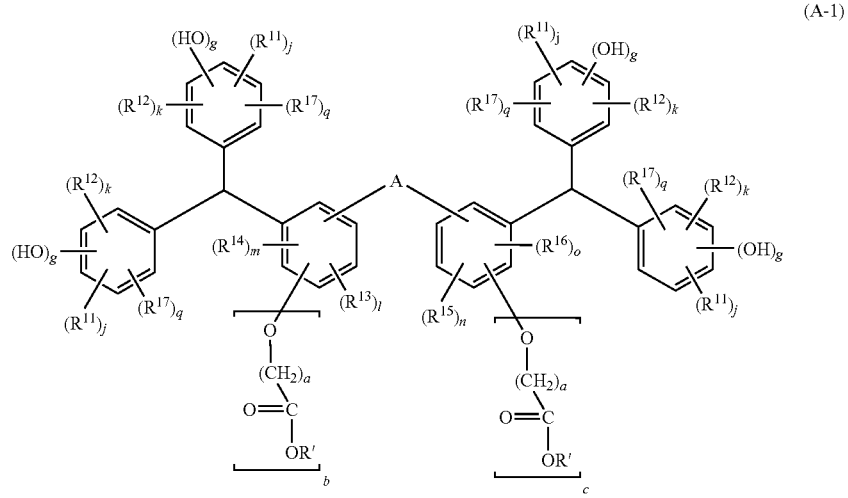

[wherein, in said formula (A-1), R' represents a hydrogen atom or an acid-dissociable, dissolution-inhibiting group, provided that at least one of a plurality of said R' groups is an acid-dissociable, dissolution-inhibiting group, wherein the acid-dissociable, dissolution-inhibiting group is at least one selected from the group consisting of a tertiary alkyloxycarbonyl group, an alkoxycarbonylalkyl group, an alkoxyalkyl group, and a cyclic ether group;

$R^{11}$ to $R^{17}$ each represent, independently, an alkyl group of 1 to 10 carbon atoms or an aromatic hydrocarbon group, which may include a hetero atom within a structure thereof; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group;]

[Formula 2]

[Formula 2]

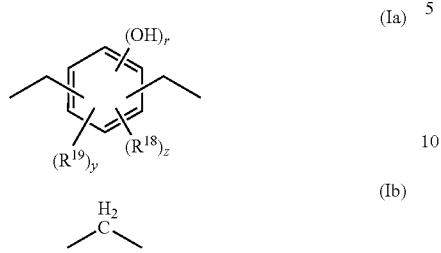

[wherein, in said formula (Ia), $R^{18}$ and $R^{19}$ each represent, independently, an alkyl group of 1 to 10 carbon atoms or an aromatic hydrocarbon group, which may include a hetero atom within a structure thereof; and r, y and z each represent, independently, an integer of 0 or greater, provided that r+y+z is not greater than 4].

2. A compound according to claim 1, represented by a general formula (A-2) shown below:

[Formula 3]

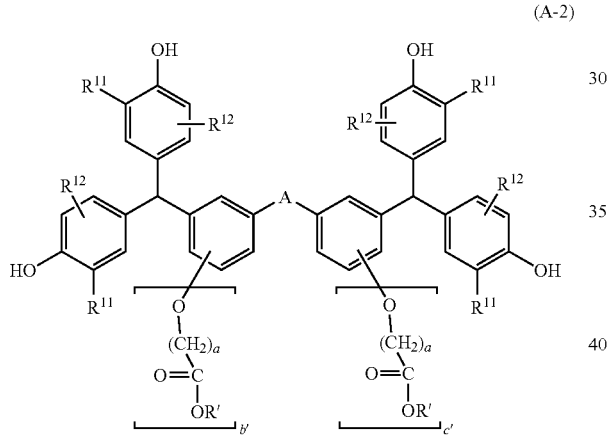

[wherein, in said formula (A-2), R' represents a hydrogen atom or an acid-dissociable, dissolution-inhibiting group, provided that at least one of a plurality of said R' groups is an acid-dissociable, dissolution-inhibiting group, wherein the acid-dissociable, dissolution-inhibiting group is at least one selected from the group consisting of a tertiary alkyloxycarbonyl group, an alkoxycarbonylalkyl group, an alkoxyalkyl group, and a cyclic ether group;

$R^{11}$ to $R^{12}$ each represent, independently, an alkyl group of 1 to 10 carbon atoms or an aromatic hydrocarbon group, which may include a hetero atom within a structure thereof; a represents an integer from 1 to 3; b' represents an integer from 1 to 4; c' represents an integer from 1 to 4; and A represents a group represented by said general formula (Ia) shown above, a group represented by said general formula (Ib) shown above, or an aliphatic cyclic group].

3. A positive resist composition comprising a base material component (A) that exhibits increased alkali solubility under action of acid, and an acid generator component (B) that generates acid upon irradiation, wherein said base material component (A) comprises a compound (A1) represented by a general formula (A-1) shown below:

[Formula 4]

[wherein, in said formula (A-1), R' represents a hydrogen atom or an acid-dissociable, dissolution-inhibiting group, provided that at least one of a plurality of said R' groups is an acid-dissociable, dissolution-inhibiting group, wherein the acid-dissociable, dissolution-inhibiting group is at least one selected from the group consisting of a tertiary alkyloxycarbonyl group, an alkoxycarbonylalkyl group, an alkoxyalkyl group, and a cyclic ether group;

wherein the acid-dissociable, dissolution-inhibiting group is at least one member selected from the group consisting of tertiary alkyloxycarbonyl groups, alkoxycarbonylalkyl groups, alkoxyalkyl groups, and cyclic ether groups;

$R^{11}$ to $R^{17}$ each represent, independently, an alkyl group of 1 to 10 carbon atoms or an aromatic hydrocarbon group, which may include a hetero atom within a structure thereof; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group:]

[Formula 5]

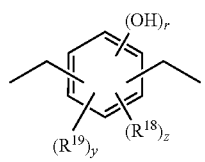

(Ia)

(Ib)

[wherein, in said formula (Ia), $R^{18}$ and $R^{19}$ each represent, independently, an alkyl group of 1 to 10 carbon atoms or an aromatic hydrocarbon group, which may include a hetero atom within a structure thereof; and r, y and z each represent, independently, an integer of 0 or greater, provided that r+y+z is not greater than 4].

4. A positive resist composition according to claim 3, wherein said compound (A1) is a compound represented by a general formula (A-2) shown below:

[Formula 6]

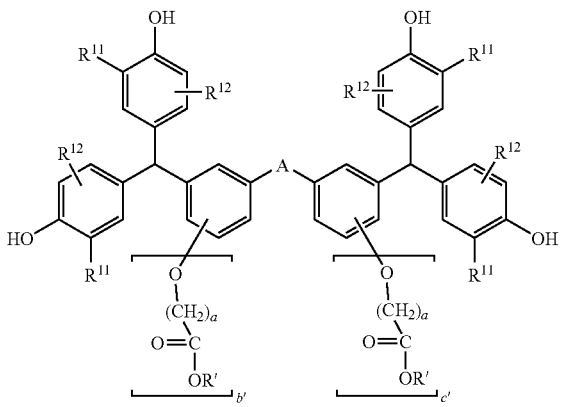

(A-2)

[wherein, in said formula (A-2), R' represents a hydrogen atom or an acid-dissociable, dissolution-inhibiting group, provided that at least one of a plurality of said R' groups is an acid-dissociable, dissolution-inhibiting group, wherein the acid-dissociable, dissolution-inhibiting group is at least one selected from the group consisting of a tertiary alkyloxycarbonyl group, an alkoxycarbonylalkyl group, an alkoxyalkyl group, and a cyclic ether group;

$R^{11}$ to $R^{12}$ each represent, independently, an alkyl group of 1 to 10 carbon atoms or an aromatic hydrocarbon group, which may include a hetero atom within a structure thereof; a represents an integer from 1 to 3; b' represents an integer from 1 to 4; c' represents an integer from 1 to 4; and A represents a group represented by said general formula (Ia) shown above, a group represented by said general formula (Ib) shown above, or an aliphatic cyclic group].

5. A positive resist composition according to claim 3, further comprising a nitrogen-containing organic compound (D).

6. A method for forming a resist pattern, comprising the steps of: forming a resist film on a substrate using a positive resist composition according to claim 3, exposing said resist film, and developing said resist film to form a resist pattern.

7. A method for forming a resist pattern, comprising the steps of: forming a resist film on a substrate using a positive resist composition according to claim 5, exposing said resist film, and developing said resist film to form a resist pattern.

8. A compound represented by a general formula (I) shown below:

[Formula 7]

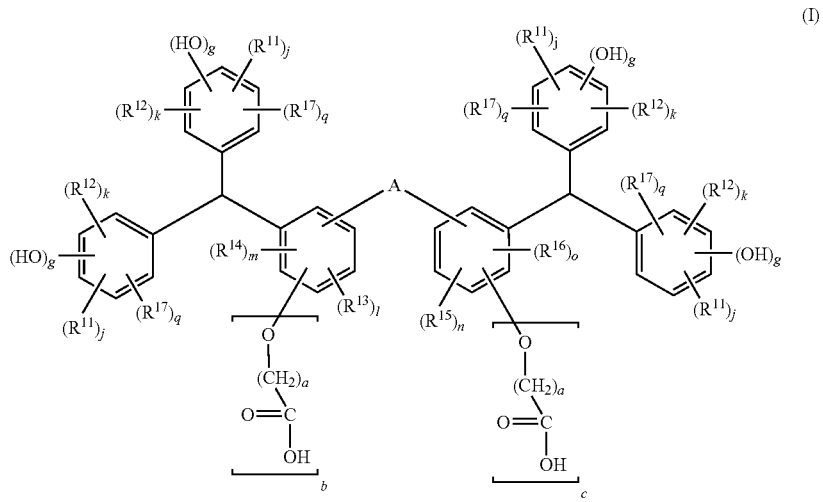

(I)

[wherein, in said formula (I), $R^{11}$ to $R^{17}$ each represent, independently, an alkyl group of 1 to 10 carbon atoms or an aromatic hydrocarbon group, which may include a hetero atom within a structure thereof; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group:]

[Formula 8]

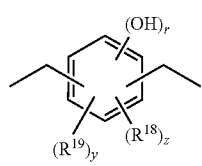

(Ia)

(Ib)

[wherein, in said formula (Ia), $R^{18}$ and $R^{19}$ each represent, independently, an alkyl group of 1 to 10 carbon atoms or an aromatic hydrocarbon group, which may include a hetero atom within a structure thereof; and r, y and z each represent, independently, an integer of 0 or greater, provided that r+y+z is not greater than 4].

9. A compound according to claim 8, represented by a general formula (II) show below:

[Formula 9]

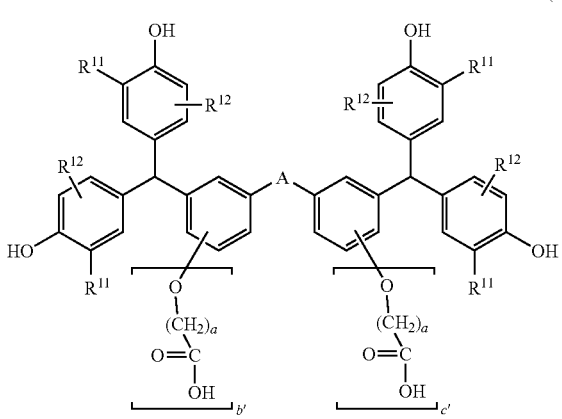

(II)

[wherein, in said formula (II), $R^{11}$ to $R^{12}$ each represent, independently, an alkyl group of 1 to 10 carbon atoms or an aromatic hydrocarbon group, which may include a hetero atom within a structure thereof; a represents an integer from 1 to 3; b' represents an integer from 1 to 4; c'represents an integer from 1 to 4; and A represents a group represented by a general formula (Ia) shown below, a group represented by a general formula (Ib) shown below, or an aliphatic cyclic group:]

[Formula 10]

(Ia)

 (Ib)

[wherein, in said formula (Ia), $R^{18}$ and $R^{19}$ each represent, independently, an alkyl group of 1 to 10 carbon atoms or an aromatic hydrocarbon group, which may include a hetero atom within a structure thereof; and r, y and z each represent, independently, an integer of 0 or greater, provided that r+y+z is not greater than 4].

10. A method for producing a compound that includes:

a step of reacting a compound (I-1) represented by a general formula (I-1) shown below and a compound (I-2) represented by a general formula (I-2) shown below to obtain a compound (I-3) represented by a general formula (I-3) shown below, and a step of obtaining a compound represented by a general formula (I) shown below, via a step of reacting said compound (I-3) and a compound (I-4) represented by a general formula (I-4) shown below under acidic conditions:

Formula 11]

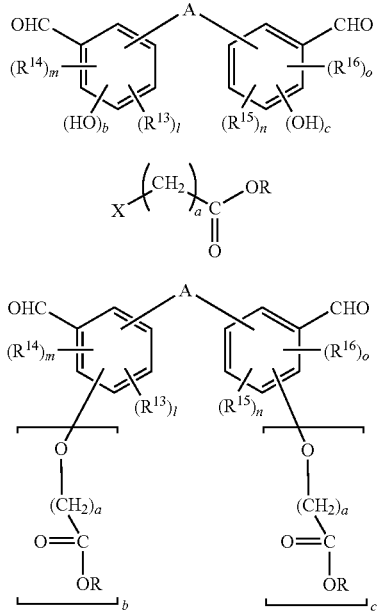

[wherein, X represents a halogen atom; R represents a protective group, $R^{13}$ to $R^{16}$ each represent, independently, an alkyl group of 1 to 10 carbon atoms or an aromatic hydrocarbon group, which may include a hetero atom within a structure thereof; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by a general formula (Ia) shown below, a group represented by a general formula (Ib) shown below, or an aliphatic cyclic group:]

[Formula 12]

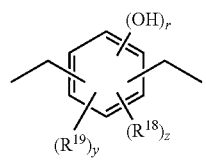 (Ia)

 (Ib)

[wherein, in said formula (Ia), $R^{18}$ and $R^{19}$ each represent, independently, an alkyl group of 1 to 10 carbon atoms or an aromatic hydrocarbon group, which may include a hetero atom within a structure thereof; and r, y and z each represent, independently, an integer of 0 or greater, provided that r+y+z is not greater than 4]

[Formula 13]

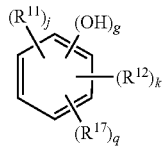 (I-4)

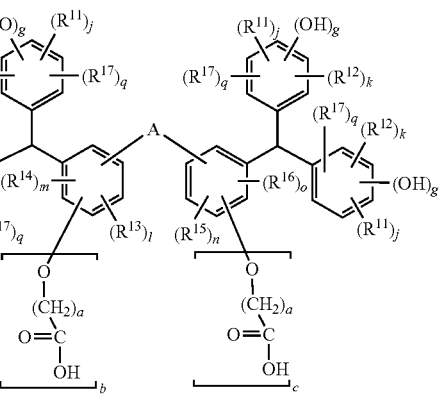 (I)

[wherein, $R^{11}$ to $R^{17}$ each represent, independently, an alkyl group of 1 to 10 carbon atoms or an aromatic hydrocarbon group, which may include a hetero atom within a structure thereof; g and j each represent, independently, an integer of 1 or greater, and k and q each represent an integer of 0 or greater, provided that g+j+k+q is not greater than 5; a represents an integer from 1 to 3; b represents an integer of 1 or greater, and l and m each represent, independently, an integer of 0 or greater, provided that b+l+m is not greater than 4; c represents an integer of 1 or greater, and n and o each represent, independently, an integer of 0 or greater, provided that c+n+o is not greater than 4; and A represents a group represented by said general formula (Ia) shown above, a group represented by said general formula (Ib) shown above, or an aliphatic cyclic group].

11. A compound according to claim 1, wherein the acid-dissociable, dissolution-inhibiting group is at least one member selected from the group represented by the general formulas (p1) or (p2) shown below;

(p1) 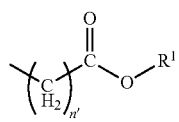
(p2) 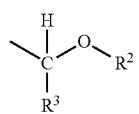
[wherein, $R^1$ and $R^2$ each represent, independently, a straight-chain, branched or cyclic alkyl group, which may include a hetero atom within the structure; $R^3$ represents a hydrogen atom or a lower alkyl group of 1 to 5 carbon atoms; and n' represents an integer from 1 to 3.]
\* \* \* \* \*

UNITED STATES PATENT AND TRADEMARK OFFICE
CERTIFICATE OF CORRECTION

PATENT NO. : 7,960,089 B2
APPLICATION NO. : 12/067255
DATED : June 14, 2011
INVENTOR(S) : Daiju Shiono et al.

Page 1 of 6

It is certified that error appears in the above-identified patent and that said Letters Patent is hereby corrected as shown below:

ON THE TITLE PAGE:

(Item 56) Col. 2, Line 8-10, Under Other Publications, delete "Kim et al., Novel Molecular........pp. 1064-1065, (2002)." and insert the same on Page 1, Col. 2, Line 9 as a new entry.

IN THE SPECIFICATIONS:

At Column 2, Line 39, After "435" insert --.--.

At Column 3, Line 9-26 Change

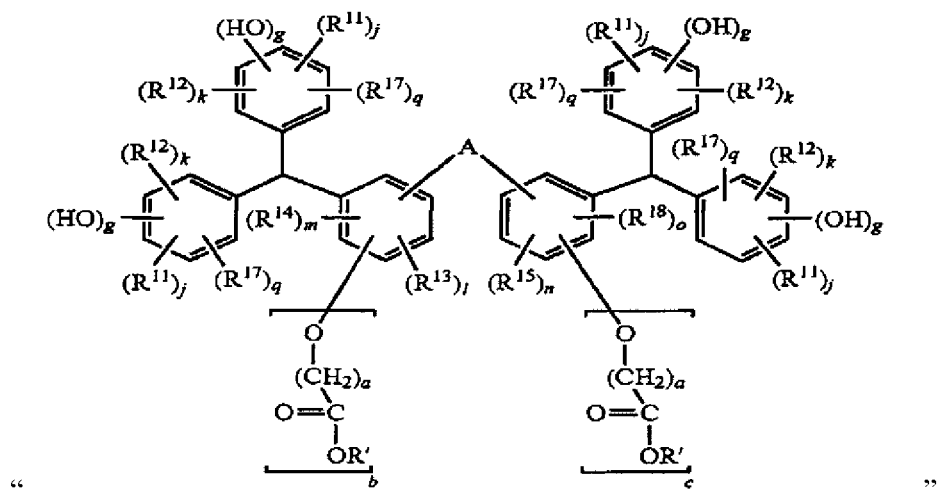

" "

Signed and Sealed this

Thirteenth Day of December, 2011

David J. Kappos
*Director of the United States Patent and Trademark Office*

CERTIFICATE OF CORRECTION (continued)
U.S. Pat. No. 7,960,089 B2

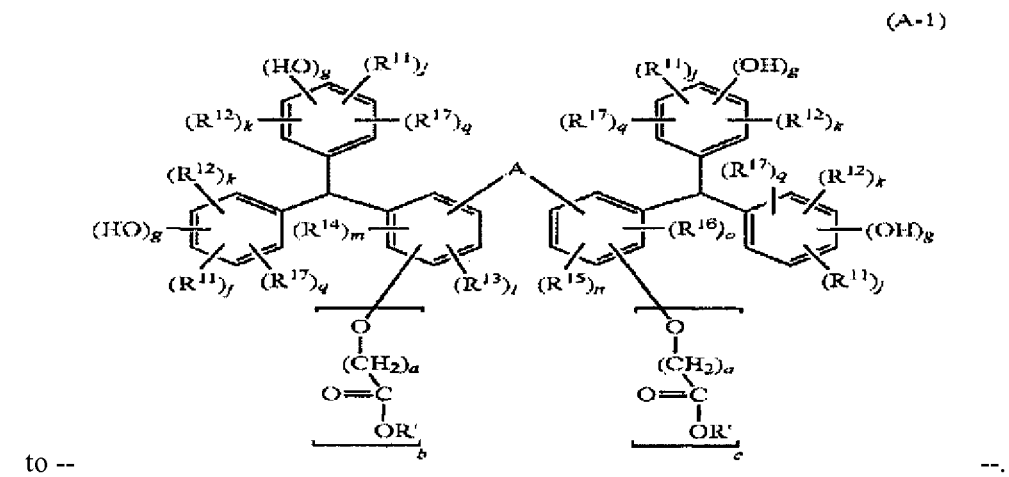

to --

At Column 4, Line 9-26

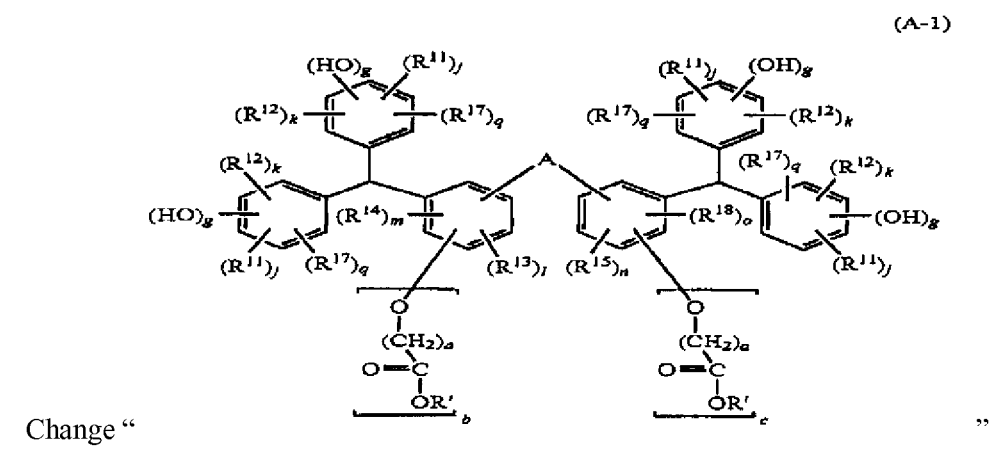

Change "

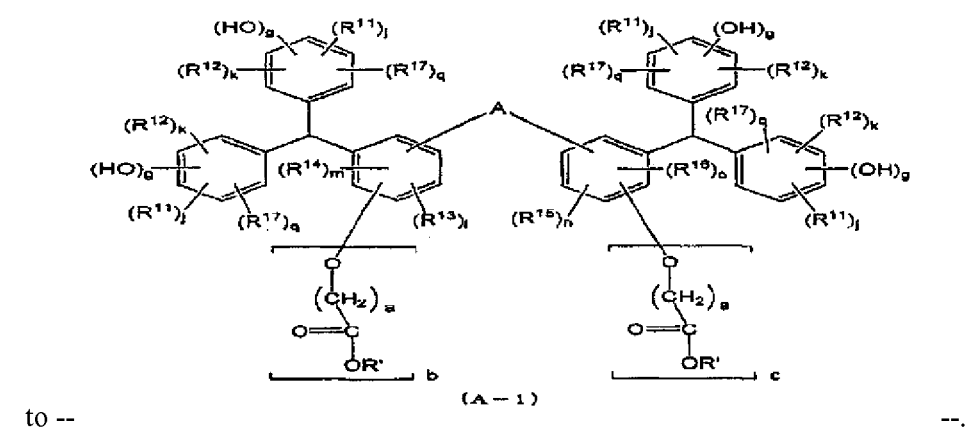

to --  --.

At Column 18, Line 1-38 (Approx.)
[Formula 16]
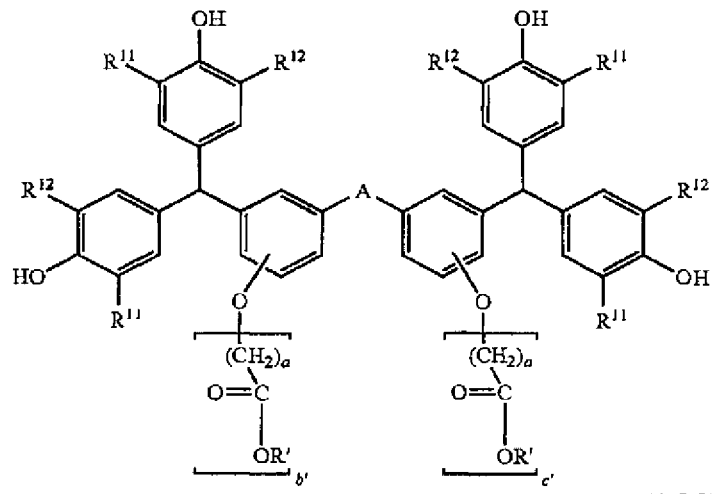
(A-2-2)
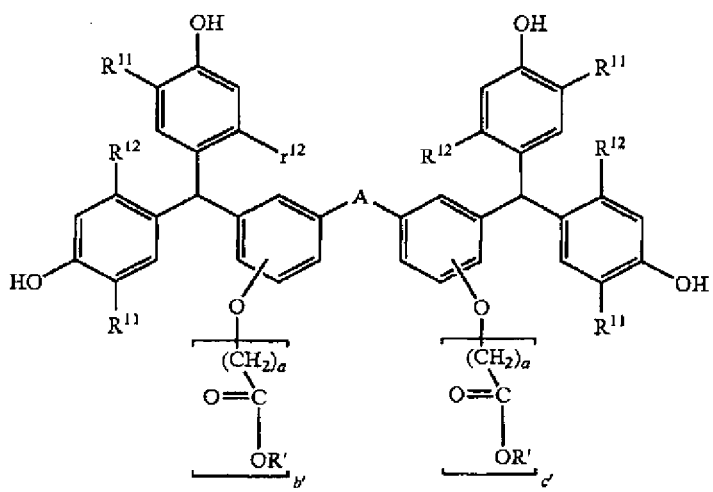
(A-2-3)
Change " "

[Formula 16]
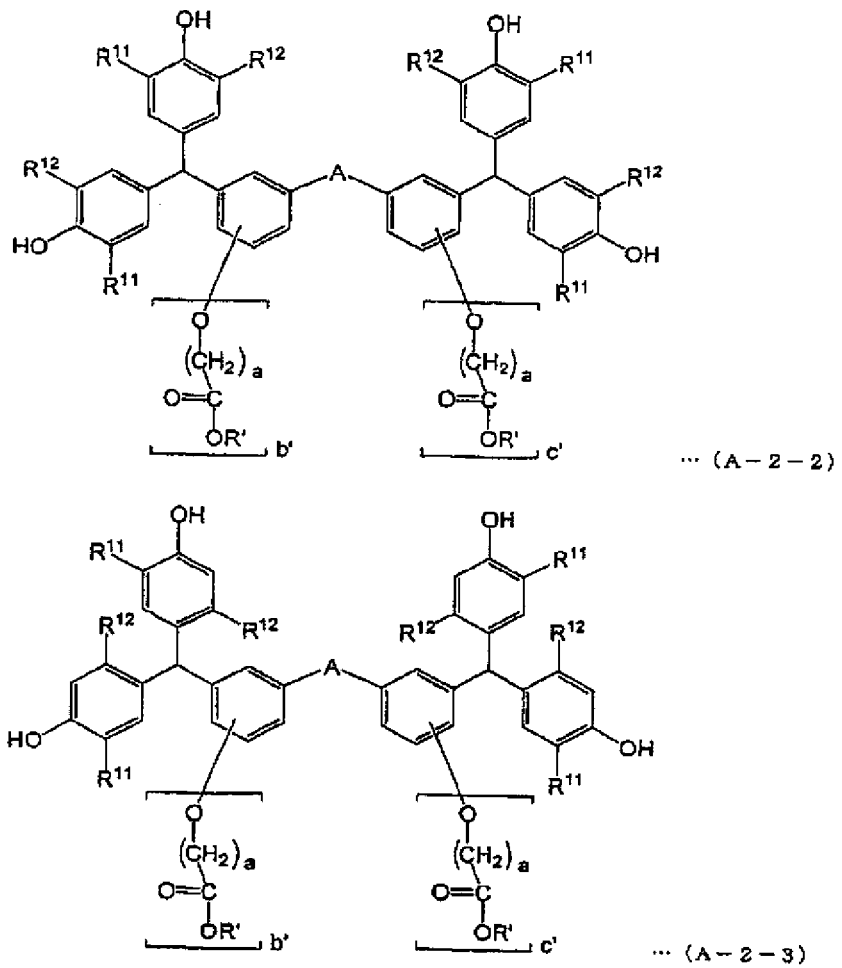
to -- --.
At Column 19, Line 16-32 (Approx.)

CERTIFICATE OF CORRECTION (continued)
U.S. Pat. No. 7,960,089 B2

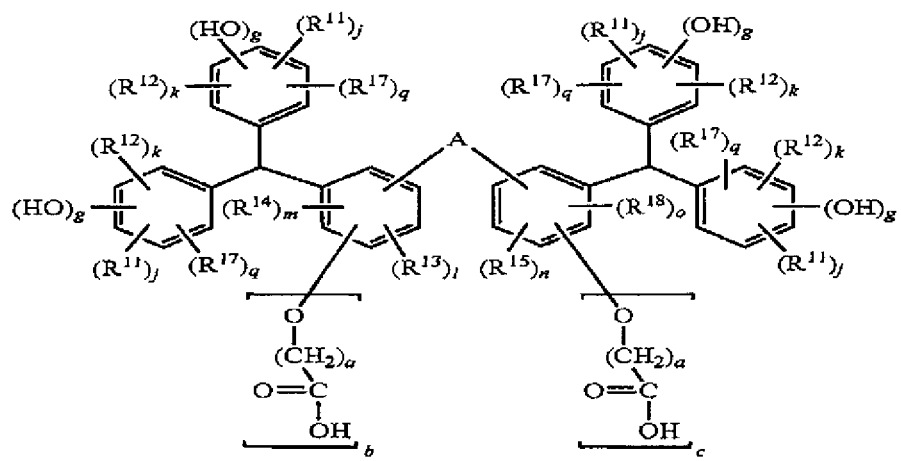

Change "

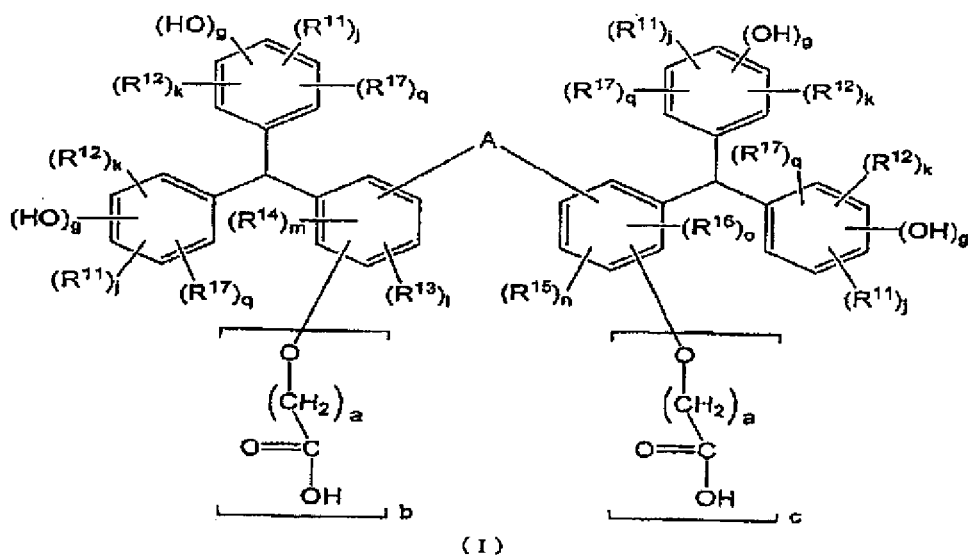

to --           --.

At Column 24, Line 20

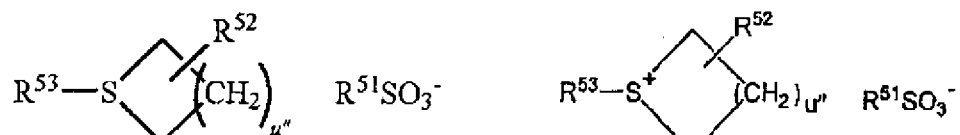

Change "                                          " to --                              --.

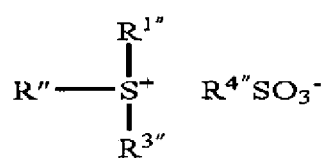

At Column 26, Line 25-29 Change "                                      "

to -- 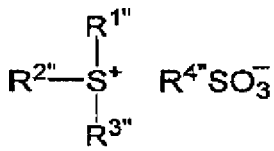 --.

At Column 27, Lines 52-53 Change "diphenyl)iodonium" to --diphenyliodonium--.

At Column 33, Line 28-30 (Approx.) Change " 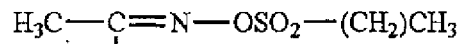 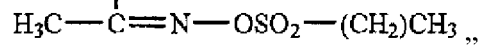 "

to -- 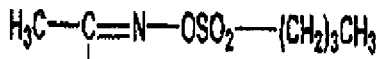 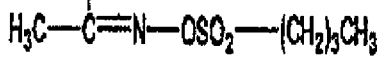 --.

At Column 34, Line 24 Change "tri-n-heptylarnine," to --tri-n-heptylamine,--.

At Column 41, Line 7-8 Change "tetrahydropyranyl" to --tetrahydrofuranyl--.

At Column 41, Line 37 After "above for" insert --$R^{11}$, $R^{12}$, $R^{17}$,--.

At Column 52, Line 56 (Approx.) Change "(5))" to --(5)--.

At Column 56, Line 60 (Approx.) Change "2925 $cm^{-i}$" to --2925 $cm^{-1}$--.

IN THE CLAIMS:

At Column 67, Line 1, In Claim 8, after "shown" insert --below:--.

At Column 67, Line 2, In Claim 8, after "shown" change " [Formula 7] " to --[Formula 7]--.

In Column 67, Line 36, In Claim 8, change "b+l +m" to --b+l+m--.

In Column 68, Line 53, In Claim 9, change "c'represents" to --c' represents--.